United States Patent
Burnett, Jr. et al.

[11] Patent Number: 6,103,475
[45] Date of Patent: Aug. 15, 2000

[54] EXCITATORY AMINO ACID RECEPTOR PROTEIN EXPRESSION TESTING METHODS

[75] Inventors: James Paul Burnett, Jr.; Nancy Gail Mayne; Robert Leon Sharp; Yvonne Marie Snyder, all of Indianapolis, Ind.

[73] Assignee: Eli Lilly and Company, Indianapolis, Ind.

[21] Appl. No.: 09/258,523

[22] Filed: Feb. 26, 1999

Related U.S. Application Data

[62] Division of application No. 08/337,797, Nov. 14, 1994, Pat. No. 6,017,697.

[51] Int. Cl.$^7$ ................................................ C12Q 1/68
[52] U.S. Cl. .................. 435/6; 435/69.1; 514/2; 514/44
[58] Field of Search .............. 435/6, 69.1; 514/2, 514/44

[56] References Cited

U.S. PATENT DOCUMENTS

| | | | |
|---|---|---|---|
| 5,521,297 | 5/1996 | Daggett et al. | 536/23.5 |
| 5,807,689 | 9/1998 | Daggett et al. | 435/78 |

*Primary Examiner*—Ardin H. Marschel
*Attorney, Agent, or Firm*—Alexander Wilson

[57] ABSTRACT

This invention describes a novel human glutamate receptors, designated mGluR2. This invention also encompasses nucleic acids encoding this receptor, or a fragment thereof, as well as methods employing this receptor and the nucleic acid compounds.

3 Claims, 2 Drawing Sheets

EXCITATORY AMINO ACID RECEPTOR PROTEIN EXPRESSION TESTING METHODS

This application is a division of application Ser. No. 08/337,797, filed Nov. 14, 1994, now U.S. Pat. No. 6,017, 697.

BACKGROUND OF THE INVENTION

In the mammalian central nervous system (CNS), the transmission of nerve impulses is controlled by the interaction between a neurotransmitter, that is released by a sending neuron, and a surface receptor on a receiving neuron, which causes excitation of this receiving neuron. L-Glutamate, which is the most abundant neurotransmitter in the CNS, mediates the :major excitatory pathway in mammals, and is referred to as an excitatory amino acid (EAA). The receptors that respond to glutamate are called excitatory amino acid receptors (EAA receptors). See Watkins & Evans, *Annual Reviews in Pharmacology and Toxicology,* 21:165 (1981); Monaghan, Bridges, and Cotman, *Annual Reviews in Pharmacology and Toxicoloay,* 29:365 (1989); Watkins, Krogsgaard-Larsen, and Honore, *Transactions in Pharmaceutical Science,* 11:25 (1990). The excitatory amino acids are of great physiological importance, playing a role in a variety of physiological processes, such as long-term potentiation (learning and memory), the development of synaptic plasticity, motor control, respiration, cardiovascular regulation, and sensory perception.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA).

The second general type of receptor is the G-protein or second messenger-linked "metabotropic" excitatory amino acid receptor. This second type is coupled to multiple second messenger systems that lead to enhanced phosphoinositide hydrolysis, activation of phospholipase D, increases or decreases in cAMP formation, and changes in ion channel function. Schoepp and Conn, *Trends in Pharmacological Science,* 14:13 (1993). Both types of receptors appear not only to mediate normal synaptic transmission along excitatory pathways, but also participate in the modification of synaptic connections during development and throughout life. Schoepp, Bockaert, and Sladeczek, *Trends in Pharmacological Science,* 11:508 (1990); McDonald and Johnson, *Brain Research Reviews,* 15:41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

The metabotropic glutamate receptors are a highly heterogeneous family of glutamate receptors that are linked to multiple second-messenger pathways. These receptors function to modulate the presynaptic release of glutamate, and the postsynaptic sensitivity of the neuronal cell to glutamate excitation. Agonists and antagonists of these receptors may be useful for the treatment of acute and chronic neurodegenerative conditions, and as antipsychotic, anticonvulsant, analgesic, anxiolytic, antidepressant, and anti-emetic agents.

The present invention provides an additional human excitatory amino acid receptor, designated mGluR2, to those previously known. The characterization and treatment of physiological disorders is hereby furthered.

SUMMARY OF THE INVENTION

This invention provides an isolated amino acid compound useful as a human metabotropic glutamate receptor, said compound comprising the amino acid sequence

```
Met Gly Ser Leu Leu Ala Leu Leu Ala Leu Leu Pro Leu Trp Gly Ala
 1               5                  10                  15

Val Ala Glu Gly Pro Ala Lys Lys Val Leu Thr Leu Glu Gly Asp Leu
                20                  25                  30

Val Leu Gly Gly Leu Phe Pro Val His Gln Lys Gly Gly Pro Ala Glu
            35                  40                  45

Asp Cys Gly Pro Val Asn Glu His Arg Gly Ile Gln Arg Leu Glu Ala
        50                  55                  60

Met Leu Phe Ala Leu Asp Arg Ile Asn Arg Asp Pro His Leu Leu Pro
 65                 70                  75                  80

Gly Val Arg Leu Gly Ala His Ile Leu Asp Ser Cys Ser Lys Asp Thr
                85                  90                  95

His Ala Leu Glu Gln Ala Leu Asp Phe Val Arg Ala Ser Leu Ser Arg
               100                 105                 110

Gly Ala Asp Gly Ser Arg His Ile Cys Pro Asp Gly Ser Tyr Ala Thr
           115                 120                 125

His Gly Asp Ala Pro Thr Ala Ile Thr Gly Val Ile Gly Gly Ser Tyr
       130                 135                 140

Ser Asp Val Ser Ile Gln Val Ala Asn Leu Leu Arg Leu Phe Gln Ile
```

-continued

```
145                 150                 155                 160
Pro Gln Ile Ser Tyr Ala Ser Thr Ser Ala Lys Leu Ser Asp Lys Ser
                165                 170                 175
Arg Tyr Asp Tyr Phe Ala Arg Thr Val Pro Asp Phe Phe Gln Ala
                180                 185                 190
Lys Ala Met Ala Glu Ile Leu Arg Phe Phe Asn Trp Thr Tyr Val Ser
                195                 200                 205
Thr Val Ala Ser Glu Gly Asp Tyr Gly Glu Thr Gly Ile Glu Ala Phe
    210                 215                 220
Glu Leu Glu Ala Arg Ala Arg Asn Ile Cys Val Ala Thr Ser Glu Lys
225                 230                 235                 240
Val Gly Arg Ala Met Ser Arg Ala Ala Phe Glu Gly Val Val Arg Ala
                245                 250                 255
Leu Leu Gln Lys Pro Ser Ala Arg Val Ala Val Leu Phe Thr Arg Ser
                260                 265                 270
Glu Asp Ala Arg Glu Leu Leu Ala Ala Ser Gln Arg Leu Asn Ala Ser
                275                 280                 285
Phe Thr Trp Val Ala Ser Asp Gly Trp Gly Ala Leu Glu Ser Val Val
            290                 295                 300
Ala Gly Ser Glu Gly Ala Ala Glu Gly Ala Ile Thr Ile Glu Leu Ala
305                 310                 315                 320
Ser Tyr Pro Ile Ser Asp Phe Ala Ser Tyr Phe Gln Ser Leu Asp Pro
                325                 330                 335
Trp Asn Asn Ser Arg Asn Pro Trp Phe Arg Glu Phe Trp Glu Gln Arg
                340                 345                 350
Phe Arg Cys Ser Phe Arg Gln Arg Asp Cys Ala Ala His Ser Leu Arg
                355                 360                 365
Ala Val Pro Phe Glu Gln Glu Ser Lys Ile Met Phe Val Val Asn Ala
    370                 375                 380
Val Tyr Ala Met Ala His Ala Leu His Asn Met His Arg Ala Leu Cys
385                 390                 395                 400
Pro Asn Thr Thr Arg Leu Cys Asp Ala Met Arg Pro Val Asn Gly Arg
                405                 410                 415
Arg Leu Tyr Lys Asp Phe Val Leu Asn Val Lys Phe Asp Ala Pro Phe
                420                 425                 430
Arg Pro Ala Asp Thr His Asn Glu Val Arg Phe Asp Arg Phe Gly Asp
                435                 440                 445
Gly Ile Gly Arg Tyr Asn Ile Phe Thr Tyr Leu Arg Ala Gly Ser Gly
    450                 455                 460
Arg Tyr Arg Tyr Gln Lys Val Gly Tyr Trp Ala Glu Gly Leu Thr Leu
465                 470                 475                 480
Asp Thr Ser Leu Ile Pro Trp Ala Ser Pro Ser Ala Gly Pro Leu Pro
                485                 490                 495
Ala Ser Arg Cys Ser Glu Pro Cys Leu Gln Asn Glu Val Lys Ser Val
                500                 505                 510
Gln Pro Gly Glu Val Cys Cys Trp Leu Cys Ile Pro Cys Gln Pro Tyr
                515                 520                 525
Glu Tyr Arg Leu Asp Glu Phe Thr Cys Ala Asp Cys Gly Leu Gly Tyr
                530                 535                 540
Trp Pro Asn Ala Ser Leu Thr Gly Cys Phe Glu Leu Pro Gln Glu Tyr
545                 550                 555                 560
Ile Arg Trp Gly Asp Ala Trp Ala Val Gly Pro Val Thr Ile Ala Cys
                565                 570                 575
```

-continued

```
Leu Gly Ala Leu Ala Thr Leu Phe Val Leu Gly Val Phe Val Arg His
            580                 585                 590
Asn Ala Thr Pro Val Val Lys Ala Ser Gly Arg Glu Leu Cys Tyr Ile
            595                 600                 605
Leu Leu Gly Gly Val Phe Leu Cys Tyr Cys Met Thr Phe Ile Phe Ile
    610                 615                 620
Ala Lys Pro Ser Thr Gly Val Cys Ala Leu Arg Arg Leu Gly Val Gly
625                 630                 635                 640
Thr Ala Phe Ser Val Cys Tyr Ser Ala Leu Leu Thr Lys Thr Asn Arg
            645                 650                 655
Ile Ala Arg Ile Phe Gly Ala Arg Glu Gly Ala Gln Arg Pro Arg
            660                 665                 670
Phe Ile Ser Pro Ala Ser Gln Val Ala Ile Cys Leu Ala Leu Ile Ser
            675                 680                 685
Gly Gln Leu Leu Ile Val Val Ala Trp Leu Val Val Glu Ala Pro Gly
    690                 695                 700
Thr Gly Lys Glu Thr Ala Pro Glu Arg Arg Glu Val Val Thr Leu Arg
705                 710                 715                 720
Cys Asn His Arg Asp Ala Ser Met Leu Gly Ser Leu Ala Tyr Asn Val
            725                 730                 735
Leu Leu Ile Ala Leu Cys Thr Leu Tyr Ala Phe Lys Thr Arg Lys Cys
            740                 745                 750
Pro Glu Asn Phe Asn Glu Ala Lys Phe Ile Gly Phe Thr Met Tyr Thr
            755                 760                 765
Thr Cys Ile Ile Trp Leu Ala Phe Leu Pro Ile Phe Tyr Val Thr Ser
    770                 775                 780
Ser Asp Tyr Arg Val Gln Thr Thr Thr Met Cys Val Ser Val Ser Leu
785                 790                 795                 800
Ser Gly Ser Val Val Leu Gly Cys Leu Phe Ala Pro Lys Leu His Ile
            805                 810                 815
Ile Leu Phe Gln Pro Gln Lys Asn Val Val Ser His Arg Ala Pro Thr
            820                 825                 830
Ser Arg Phe Gly Ser Ala Ala Arg Ala Ser Ser Ser Leu Gly Gln
            835                 840                 845
Gly Ser Gly Ser Gln Phe Val Pro Thr Val Cys Asn Gly Arg Glu Val
    850                 855                 860
Val Asp Ser Thr Thr Ser Ser Leu
865                 870
``` hereinafter designated as SEQ ID NO:2.

The invention also provides an isolated nucleic acid compound that comprises a nucleic acid sequence which encodes for the amino acid compounds provided. Particularly this invention provides the isolated nucleic acid compound having the sequence

```
ATG GGA TCG CTG CTT GCG CTC CTG GCA CTG CTG CCG CTG TGG GGT GCT    48
Met Gly Ser Leu Leu Ala Leu Leu Ala Leu Leu Pro Leu Trp Gly Ala
 1               5                  10                  15

GTG GCT GAG GGC CCA GCC AAG AAG GTG CTG ACC CTG GAG GGA GAC TTG    96
Val Ala Glu Gly Pro Ala Lys Lys Val Leu Thr Leu Glu Gly Asp Leu
                20                  25                  30

GTG CTG GGT GGG CTG TTC CCA GTG CAC CAG AAG GGC GGC CCA GCA GAG   144
Val Leu Gly Gly Leu Phe Pro Val His Gln Lys Gly Gly Pro Ala Glu
                35                  40                  45

GAC TGT GGT CCT GTC AAT GAG CAC CGT GGC ATC CAG CGC CTG GAG GCC   192
Asp Cys Gly Pro Val Asn Glu His Arg Gly Ile Gln Arg Leu Glu Ala
                50                  55                  60
```

-continued

```
ATG CTT TTT GCA CTG GAC CGC ATC AAC CGT GAC CCG CAC CTG CTG CCT    240
Met Leu Phe Ala Leu Asp Arg Ile Asn Arg Asp Pro His Leu Leu Pro
 65              70                  75                  80

GGC GTG CGC CTG GGT GCA CAC ATC CTC GAC AGT TGC TCC AAG GAC ACA    288
Gly Val Arg Leu Gly Ala His Ile Leu Asp Ser Cys Ser Lys Asp Thr
                 85                  90                  95

CAT GCG CTG GAG CAG GCA CTG GAC TTT GTG CGT GCC TCA CTC AGC CGT    336
His Ala Leu Glu Gln Ala Leu Asp Phe Val Arg Ala Ser Leu Ser Arg
            100                 105                 110

GGT GCT GAT GGC TCA CGC CAC ATC TGC CCC GAC GGC TCT TAT GCG ACC    384
Gly Ala Asp Gly Ser Arg His Ile Cys Pro Asp Gly Ser Tyr Ala Thr
        115                 120                 125

CAT GGT GAT GCT CCC ACT GCC ATC ACT GGT GTT ATT GGC GGT TCC TAC    432
His Gly Asp Ala Pro Thr Ala Ile Thr Gly Val Ile Gly Gly Ser Tyr
    130                 135                 140

AGT GAT GTC TCC ATC CAG GTG GCC AAC CTC TTG AGG CTA TTT CAG ATC    480
Ser Asp Val Ser Ile Gln Val Ala Asn Leu Leu Arg Leu Phe Gln Ile
145                 150                 155                 160

CCA CAG ATT AGC TAC GCC TCT ACC AGT GCC AAG CTG AGT GAC AAG TCC    528
Pro Gln Ile Ser Tyr Ala Ser Thr Ser Ala Lys Leu Ser Asp Lys Ser
                165                 170                 175

CGC TAT GAC TAC TTT GCC CGC ACA GTG CCT CCT GAC TTC TTC CAA GCC    576
Arg Tyr Asp Tyr Phe Ala Arg Thr Val Pro Pro Asp Phe Phe Gln Ala
            180                 185                 190

AAG GCC ATG GCT GAG ATT CTC CGC TTC TTC AAC TGG ACC TAT GTG TCC    624
Lys Ala Met Ala Glu Ile Leu Arg Phe Phe Asn Trp Thr Tyr Val Ser
        195                 200                 205

ACT GTG GCG TCT GAG GGC GAC TAT GGC GAG ACA GGC ATT GAG GCC TTT    672
Thr Val Ala Ser Glu Gly Asp Tyr Gly Glu Thr Gly Ile Glu Ala Phe
    210                 215                 220

GAG CTA GAG GCT CGT GCC CGC AAC ATC TGT GTG GCC ACC TCG GAG AAA    720
Glu Leu Glu Ala Arg Ala Arg Asn Ile Cys Val Ala Thr Ser Glu Lys
225                 230                 235                 240

GTG GGC CGT GCC ATG AGC CGC GCG GCC TTT GAG GGT GTG GTG CGA GCC    768
Val Gly Arg Ala Met Ser Arg Ala Ala Phe Glu Gly Val Val Arg Ala
                245                 250                 255

CTG CTG CAG AAG CCC AGT GCC CGC GTG GCT GTC CTG TTC ACC CGT TCT    816
Leu Leu Gln Lys Pro Ser Ala Arg Val Ala Val Leu Phe Thr Arg Ser
            260                 265                 270

GAG GAT GCC CGG GAG CTG CTT GCT GCC AGC CAG CGC CTC AAT GCC AGC    864
Glu Asp Ala Arg Glu Leu Leu Ala Ala Ser Gln Arg Leu Asn Ala Ser
        275                 280                 285

TTC ACC TGG GTG GCC AGT GAT GGT TGG GGG GCC CTG GAG AGT GTG GTG    912
Phe Thr Trp Val Ala Ser Asp Gly Trp Gly Ala Leu Glu Ser Val Val
    290                 295                 300

GCA GGC AGT GAG GGG GCT GCT GAG GGT GCT ATC ACC ATC GAG CTG GCC    960
Ala Gly Ser Glu Gly Ala Ala Glu Gly Ala Ile Thr Ile Glu Leu Ala
305                 310                 315                 320

TCC TAC CCC ATC AGT GAC TTT GCC TCC TAC TTC CAG AGC CTG GAC CCT   1008
Ser Tyr Pro Ile Ser Asp Phe Ala Ser Tyr Phe Gln Ser Leu Asp Pro
                325                 330                 335

TGG AAC AAC AGC CGG AAC CCC TGG TTC CGT GAA TTC TGG GAG CAG AGG   1056
Trp Asn Asn Ser Arg Asn Pro Trp Phe Arg Glu Phe Trp Glu Gln Arg
            340                 345                 350

TTC CGC TGC AGC TTC CGG CAG CGA GAC TGC GCA GCC CAC TCT CTC CGG   1104
Phe Arg Cys Ser Phe Arg Gln Arg Asp Cys Ala Ala His Ser Leu Arg
        355                 360                 365

GCT GTG CCC TTT GAG CAG GAG TCC AAG ATC ATG TTT GTG GTC AAT GCA   1152
Ala Val Pro Phe Glu Gln Glu Ser Lys Ile Met Phe Val Val Asn Ala
    370                 375                 380
```

```
GTG TAC GCC ATG GCC CAT GCG CTC CAC AAC ATG CAC CGT GCC CTC TGC   1200
Val Tyr Ala Met Ala His Ala Leu His Asn Met His Arg Ala Leu Cys
385                 390                 395                 400

CCC AAC ACC ACC CGG CTC TGT GAC GCG ATG CGG CCA GTT AAC GGG CGC   1248
Pro Asn Thr Thr Arg Leu Cys Asp Ala Met Arg Pro Val Asn Gly Arg
                405                 410                 415

CGC CTC TAC AAG GAC TTT GTG CTC AAC GTC AAG TTT GAT GCC CCC TTT   1296
Arg Leu Tyr Lys Asp Phe Val Leu Asn Val Lys Phe Asp Ala Pro Phe
            420                 425                 430

CGC CCA GCT GAC ACC CAC AAT GAG GTC CGC TTT GAC CGC TTT GGT GAT   1344
Arg Pro Ala Asp Thr His Asn Glu Val Arg Phe Asp Arg Phe Gly Asp
                435                 440                 445

GGT ATT GGC CGC TAC AAC ATC TTC ACC TAT CTG CGT GCA GGC AGT GGG   1392
Gly Ile Gly Arg Tyr Asn Ile Phe Thr Tyr Leu Arg Ala Gly Ser Gly
        450                 455                 460

CGC TAT CGC TAC CAG AAG GTG GGC TAC TGG GCA GAA GGC TTG ACT CTG   1440
Arg Tyr Arg Tyr Gln Lys Val Gly Tyr Trp Ala Glu Gly Leu Thr Leu
465                 470                 475                 480

GAC ACC AGC CTC ATC CCA TGG GCC TCA CCC TCA GCC GGC CCC CTG CCC   1488
Asp Thr Ser Leu Ile Pro Trp Ala Ser Pro Ser Ala Gly Pro Leu Pro
                485                 490                 495

GCC TCT CGC TGC AGT GAG CCC TGC CTC CAG AAT GAG GTG AAG AGT GTG   1536
Ala Ser Arg Cys Ser Glu Pro Cys Leu Gln Asn Glu Val Lys Ser Val
                500                 505                 510

CAG CCG GGC GAA GTC TGC TGC TGG CTC TGC ATT CCG TGC CAG CCC TAT   1584
Gln Pro Gly Glu Val Cys Cys Trp Leu Cys Ile Pro Cys Gln Pro Tyr
            515                 520                 525

GAG TAC CGA TTG GAC GAA TTC ACT TGC GCT GAT TGT GGC CTG GGC TAC   1632
Glu Tyr Arg Leu Asp Glu Phe Thr Cys Ala Asp Cys Gly Leu Gly Tyr
530                 535                 540

TGG CCC AAT GCC AGC CTG ACT GGC TGC TTC GAA CTG CCC CAG GAG TAC   1680
Trp Pro Asn Ala Ser Leu Thr Gly Cys Phe Glu Leu Pro Gln Glu Tyr
545                 550                 555                 560

ATC CGC TGG GGC GAT GCC TGG GCT GTG GGA CCT GTC ACC ATC GCC TGC   1728
Ile Arg Trp Gly Asp Ala Trp Ala Val Gly Pro Val Thr Ile Ala Cys
                565                 570                 575

CTC GGT GCC CTG GCC ACC CTC TTT GTG CTG GGT GTC TTT GTG CGG CAC   1776
Leu Gly Ala Leu Ala Thr Leu Phe Val Leu Gly Val Phe Val Arg His
                580                 585                 590

AAT GCC ACA CCA GTG GTC AAG GCC TCA GGT CGG GAG CTC TGC TAC ATC   1824
Asn Ala Thr Pro Val Val Lys Ala Ser Gly Arg Glu Leu Cys Tyr Ile
                595                 600                 605

CTG CTG GGT GGT GTC TTC CTC TGC TAC TGC ATG ACC TTC ATC TTC ATT   1872
Leu Leu Gly Gly Val Phe Leu Cys Tyr Cys Met Thr Phe Ile Phe Ile
610                 615                 620

GCC AAG CCA TCC ACG GGA GTG TGT GCC TTA CGG CGT CTT GGG GTG GGC   1920
Ala Lys Pro Ser Thr Gly Val Cys Ala Leu Arg Arg Leu Gly Val Gly
625                 630                 635                 640

ACT GCC TTC TCT GTC TGC TAC TCA GCC CTG CTC ACC AAG ACC AAC CGC   1968
Thr Ala Phe Ser Val Cys Tyr Ser Ala Leu Leu Thr Lys Thr Asn Arg
                645                 650                 655

ATT GCA CGC ATC TTC GGT GGG GCC CGG GAG GGT GCC CAG CGG CCA CGC   2016
Ile Ala Arg Ile Phe Gly Gly Ala Arg Glu Gly Ala Gln Arg Pro Arg
                660                 665                 670

TTC ATC AGT CCT GCC TCA CAG GTG GCC ATC TGC CTG GCA CTT ATC TCG   2064
Phe Ile Ser Pro Ala Ser Gln Val Ala Ile Cys Leu Ala Leu Ile Ser
            675                 680                 685

GGC CAG CTG CTC ATC GTG GTC GCC TGG CTG GTG GTG GAG GCA CCG GGC   2112
Gly Gln Leu Leu Ile Val Val Ala Trp Leu Val Val Glu Ala Pro Gly
        690                 695                 700
```

-continued

```
ACA GGC AAG GAG ACA GCC CCC GAA CGG CGG GAG GTG GTG ACA CTG CGC    2160
Thr Gly Lys Glu Thr Ala Pro Glu Arg Arg Glu Val Val Thr Leu Arg
705             710                 715                 720

TGC AAC CAC CGC GAT GCA AGT ATG TTG GGC TCG CTG GCC TAC AAT GTG    2208
Cys Asn His Arg Asp Ala Ser Met Leu Gly Ser Leu Ala Tyr Asn Val
                725                 730                 735

CTC CTC ATC GCG CTC TGC ACG CTT TAT GCC TTC AAG ACT CGC AAG TGC    2256
Leu Leu Ile Ala Leu Cys Thr Leu Tyr Ala Phe Lys Thr Arg Lys Cys
            740                 745                 750

CCC GAA AAC TTC AAC GAG GCC AAG TTC ATT GGC TTC ACC ATG TAC ACC    2304
Pro Glu Asn Phe Asn Glu Ala Lys Phe Ile Gly Phe Thr Met Tyr Thr
        755                 760                 765

ACC TGC ATC ATC TGG CTG GCA TTC TTG CCC ATC TTC TAT GTC ACC TCC    2352
Thr Cys Ile Ile Trp Leu Ala Phe Leu Pro Ile Phe Tyr Val Thr Ser
    770                 775                 780

AGT GAC TAC CGG GTA CAG ACC ACC ACC ATG TGC GTG TCA GTC AGC CTC    2400
Ser Asp Tyr Arg Val Gln Thr Thr Thr Met Cys Val Ser Val Ser Leu
785                 790                 795                 800

AGC GGC TCC GTG GTG CTT GGC TGC CTC TTT GCG CCC AAG CTG CAC ATC    2448
Ser Gly Ser Val Val Leu Gly Cys Leu Phe Ala Pro Lys Leu His Ile
                805                 810                 815

ATC CTC TTC CAG CCG CAG AAG AAC GTG GTT AGC CAC CGG GCA CCC ACC    2496
Ile Leu Phe Gln Pro Gln Lys Asn Val Val Ser His Arg Ala Pro Thr
            820                 825                 830

AGC CGC TTT GGC AGT GCT GCT GCC AGG GCC AGC TCC AGC CTT GGC CAA    2544
Ser Arg Phe Gly Ser Ala Ala Ala Arg Ala Ser Ser Ser Leu Gly Gln
        835                 840                 845

GGG TCT GGC TCC CAG TTT GTC CCC ACT GTT TGC AAT GGC CGT GAG GTG    2592
Gly Ser Gly Ser Gln Phe Val Pro Thr Val Cys Asn Gly Arg Glu Val
    850                 855                 860

GTG GAC TCG ACA ACG TCA TCG CTT TGA                                2619
Val Asp Ser Thr Thr Ser Ser Leu
865                 870
``` which is hereinafter designated as SEQ ID NO:1.

This invention also provides recombinant nucleic acid vectors comprising nucleic acids encoding SEQ ID NO:2.

This invention also encompasses recombinant DNA vectors which comprise the isolated DNA sequence which is SEQ ID NO:1.

The present invention also provides assays for determining the efficacy and adverse reaction profile of agents useful in the treatment or prevention of disorders associated with an excess or deficiency in the amount of glutamate present.

DETAILED DESCRIPTION AND PREFERRED EMBODIMENTS

Figure 1:
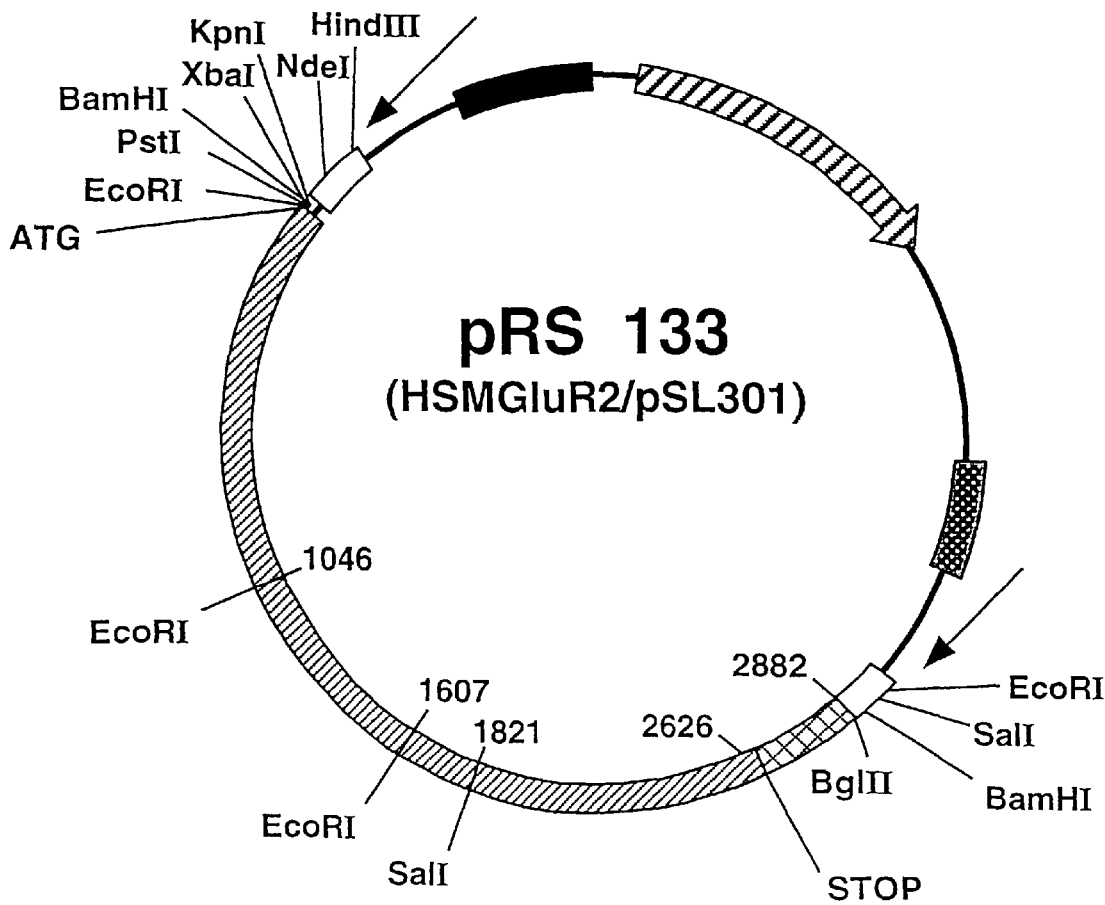
FIG. 1 is a restriction and function map of the plasmid pRS133. The arc having the wider line indicates that portion of the plasmid which corresponds to SEQ ID NO:1, infra. The arrow delineates that region of the insert which encodes the protein of SEQ ID NO:2 with the direction of the arrow indicating the natural order of transcription from the 5' end to the 3' end. The designation "ORI" refers to the plasmid origin of replication. The designation "fl ori" refers to phage f1-derived origin of replication. The designation "amp$^r$" refers to the gene encoding ampicillin resistance. The designations "T7" and "T3" refer to the T7 promoter and the T3 promoter, respectively.

The terms and abbreviations used in this document have their normal meanings unless otherwise designated. For example "° C" refers to degrees Celsius; "N" refers to normal or normality; "mmol" refers to millimole or millimoles; "g" refers to gram or grams; "ml" means milliliter or milliliters; "M" refers to molar or molarity; "μg" refers to microgram or micrograms; and "μl" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus").

"Base pair" or "bp" as used herein refers to DNA or RNA. The abbreviations A,C,G, and T correspond to the 5'-monophosphate forms of the deoxyribonucleosides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the ribonucleosides uracil, cytidine, guanine, and thymine, respectively when they occur in RNA molecules. In double stranded DNA, base pair may refer to a partnership of A with T or C with G. In a DNA/RNA, heteroduplex base pair may refer to a partnership of A with U or C with G. (See the definition of "complementary", infra.)

The terms "digestion" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two double stranded nucleic acid fragments (T. Maniatis, et al., supra., p. 146). Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" preceded and/or followed by letters and/or numbers. The starting plasmids herein are either commercially available, publicly available on an unrestricted basis, or can be constructed from available plasmids in accordance with published procedures.

In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter to control transcription of the inserted DNA has been incorporated.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods, such as nuclear injection, protoplast fusion or by calcium treatment using calcium chloride are summarized in J. Sambrook, et al., "Molecular Cloning: A Laboratory Manual" (1989).

The term "translation" as used herein refers to the process whereby the genetic information of messenger RNA is used to specify and direct the synthesis of a polypeptide chain.

The term "Vector" as used herein refers to a nucleic acid compound used for the transformation of cells in gene manipulation bearing polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by cutting and joining DNA molecules from different sources using restriction enzymes and ligases. The term "vector" as used herein includes Recombinant DNA cloning vectors and Recombinant DNA expression vectors.

The terms "complementary" or "complementarity" as used herein refers to pair of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA. "Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "stringency" refers to a set of hybridization conditions which may be varied in order to vary the degree of nucleic acid affinity for other nucleic acid. (See the definition of "hybridization", supra.)

The term "antigenically distinct" as used herein refers to a situation in which antibodies raised against an epitope of the proteins of the present invention, or a fragment thereof, may be used to differentiate between the proteins of the present invention and other glutamate receptor subtypes. This term may also be employed in the sense that such antibodies may be used to differentiate between the human mGluR2 receptor protein and analogous proteins derived from other species.

The term "PCR" as used herein refers to the widely-known polymerase chain reaction employing a thermally-stable polymerase.

This invention provides the protein of SEQ ID NO:2, a human metabotropic glutamate receptor, designated as a mGluR2 receptor using the nomenclature system described in D. D. Schoepp, "Glutamate receptors", *Handbook of Receptors and Channels,* Chapter 13 (S. J. Peroutka, ed., CRC Press, 1984). Based on the rat cognate of this receptor, the mGluR2 receptor is believed to be found in a large number of tissues throughout the body, including many regions of the brain such as the Golgi cells of the cerebellum. H. Ohishi, et al., *Neuroscience,* 3:1009–1018 (1993). Marked expression of mGluR2 messenger RNA is also found in the mitral cells of the accessory olfactory bulb, neurons in the external part of the anterior olfactory nucleus, and pyramidal neurons in the entorhinal and parasubicular cortical regions. The granule cells of the accessory olfactory bulb, and many pyramidal and non-pyramidal neurons in the neocortical, cingulate, retrosplenial, and subicular cortices, were moderately labeled. All of the granule cells in the dentate gyrus were also labeled moderately.

In the basal forebrain regions, moderately labeled neurons are distributed in the triangular septal nucleus, in the lateral, basolateral, and basomedial amygdaloid nuclei, and in the medial mammillary nucleus. Weakly labeled neurons are sparsely scattered in the striatum, globus pallidus, ventral pallidum, and claustrum. The subthalmic nucleus is also labeled weakly. In the thalamus, moderately labeled are distributed in the anterodorsal, antromedial, ventromedial, intralaminar, and midline nuclei; the ventrolateral part of the anteroventral nucleus and the rostral pole of the ventrolateral nucleus also contain moderately labeled neurons.

This receptor is believed to potentiate central nervous system responses and is, therefore, an important target for pharmaceutical purposes.

Skilled artisans will recognize that the proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, herein incorporated by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl

Asp, cyclohexyl

Glu, cyclohexyl

Ser, Benzyl

Thr, Benzyl

Tyr, 4-bromo carbobenzoxy

Removal of the t-butoxycarbonyl moiety (deprotection) may be accomplished with trifluoroacetic acid (TFA) in methylene chloride. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees centigrade or below, preferably $-20°$ C. for thirty minutes followed by thirty minutes at $0°$ C.

After removal of the hydrogen fluoride, the peptide/resin is washed with ether, and the peptide extracted with glacial acetic acid and then lyophilized. Purification accomplished by size-exclusion chromatography on a Sephadex G-10 (Pharmacia) column in 10% acetic acid.

The proteins of the present invention may also be produced by recombinant methods. Recombinant methods are preferred if a high yield is desired. A general method for the construction of any desired DNA sequence is provided in J. Brown, et al., *Methods in Enzymology,* 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes are used for cloning of DNA sequences in constructing the vectors of this invention.

Prokaryotes may also be employed in the production of the protein of interest. For example, the *Escherichia coli* K12 strain 294 (ATCC No. 31446) is particularly useful for the prokaryotic expression of foreign proteins. Other strains of *E. coli* which may be used (and their relevant genotypes) include the following.

| Strain | Genotype |
|---|---|
| DH5α | F⁻ (φ80dlacZΔM15), Δ(lacZYA-argF)U169 supE44, λ⁻, hsdR17($r_K^-$, $m_K^+$), recA1, endA1, gyrA96, thi-1, relA1 |
| HB101 | supE44, hsdS20($r_B^-$ $m_B^-$), recA13, ara-14, proA2 lacY1, galK2, rpsL20, xyl-5, |

-continued

| Strain | Genotype |
|---|---|
| JM109 | mt1-1, mcrB, mrr recA1, e14−(mcrA), supE44, endA1, hsdR17 ($r_K^-$, $m_K^+$), gyrA96, relA1, thi-1, Δ(lac-proAB), F′[traD36, proAB+ lacI$^q$,lacZΔM15] |
| RR1 | supE44, hsdS20($r_B^-$ $m_B^-$), ara-14 proA2, lacY1, galK2, rpsL20, xyl-5, mtl-5 |
| χ1776 | F−, ton, A53, dapD8, minA1, supE42 (glnV42), Δ(gal-uvrB)40, minB2, rfb-2, gyrA25, thyA142, oms-2, metC65, oms-1, Δ(bioH-asd)29, cycB2, cycA1, hsdR2, λ− |
| 294 | endA, thi−, hsr−, hsm$_k^+$ (U.S. Pat. No. 4,366,246) |

These strains are all commercially available from suppliers such as: Bethesda Research Laboratories, Gaithersburg, Md. 20877 and Stratagene Cloning Systems, La Jolla, Calif. 92037; or are readily available to the poblic from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra. A preferred strain of *E. coli* employed in the cloning and expression of the genes of this invention is RV308, which is available from the ATCC under accession number ARCC 31608, and is described in U.S. Pat. No. 4,551,433, issued Nov. 5, 1985.

In addition to the strains of *E. coli* discussed supra, bacilli such as *Bacillus subtilis,* other enterobacteriaceae such as *Salmonella typhimurium* or *Serratia marcescans,* and various Pseudomonas species may be used. In addition to these cram-negative bacteria, other bacteria, especially Streptomyces, spp., may be employed in the prokaryotic cloning and expression of the proteins of this invention.

Promoters suitable for use with prokaryotic hosts include the β-lactamase [vector pGX2907 (ATCC 39344) contains the replicon and β-lactamase gene] and lactose promoter systems [Chang et al., *Nature(London)*, 275:615 (1978); and Goeddel et al., *Nature(London)*, 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in *Protein Purification: From Molecular Mechanisms to Large Scale Processes,* American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the human glutamate receptor-encoding nucleic acids of the present invention. Exemplary host cells suitable for use in the present invention are listed in Table I

TABLE I

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7.1 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| HS-Sultan | Human Plasma Cell Plasmocytoma | ATCC CCL 1484 |
| BHK-21 | Baby Hamster Kidney | ATCC CCL 10 |

An especially preferred cell line employed in this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-β-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See, e.g., J. Schimke, *Cell,* 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedings of the National Academy of Sciences (USA),* 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

An especially preferred expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A most preferred expression vector employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. No. 5,242,688, issued Sep. 7, 1993, and U.S. Pat. No. 4,992,373, issued Feb. 12, 1991, as well as co-pending U.S. patent application Ser. No. 07/368,700, all of which are herein incorporated by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclI site which may be utilized for the insertion of the gene encoding the protein of interest. The skilled artisan understands that linkers or adapters may be employed in cloning the gene of interest into this BclI site. A depiction of the plasmid phd is provided as FIG. 2 of this document. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See, e.g., J. Sambrook, et al., supra, at 3:16.30–3:16.66.

Other routes of production are well known to skilled artisans. In addition to the plasmid discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, herein incorporated by reference. Several alternate methods of expression are described in J. Sambrook, et al., supra, at 16.3–17.44.

In addition to prokaryotes and mammalian host cells, eukaryotic microbes such as yeast cultures may also be used. The imperfect fungus Saccharomyces cerevisiae, or common baker's yeast, is the most commonly used eukaryotic microorganism, although a number of other strains are commonly available. For expression in Saccharomyces sp., the plasmid YRp7 (ATCC-40053), for example, is commonly used.

See, e.g., L. Stinchcomb, et al., *Nature,* 282:39 (1979); J. Kingsman et al., *Gene,* 7:141 (1979); S. Tschemper et al., *Gene,* 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, herein incorporated by reference] or other glycolytic enzymes such as enolase [found on plasmid pAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, herein incorporated by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, herein incorporated by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from Saccharomyces cerevisiae (found in conjuction with the CYC1 promoter on plasmid YEpsec—hIlbeta ATCC 67024), also are advantageously used with yeast promoters.

Practitioners of this invention realize that, in addition to the above-mentioned expression systems, the cloned cDNA may also be employed in the production of transgenic animals in which a test mammal, usually a mouse, in which expression or overexpression of the proteins of the present invention can be assessed. The nucleic acids of the present invention may also be employed in the construction of "knockout" animals in which the expression of the native cognate of the gene is suppressed.

Skilled artisans also recognize that some alterations of SEQ ID NO:2 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone;

(b) the charge or hydrophobicity of the residue; or (c) the bulk of the side chain. Some examples of such conservative substitutions of amino acids, resulting in the production of proteins which are functional equivalents of the protein of SEQ ID NO:2 are shown in Table II, infra.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Mel | Leu, Ile |
| Phe | Met, Leu, Gyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein having a sequence which corresponds to the sequence of SEQ ID NO:2 may also be induced by alterations of the nucleic acid compounds which encodes these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within The present invention.

Other embodiments of the present invention are nucleic acid compounds which comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The gene encoding the human glutamate mGluR2 15 receptor molecule may be produced using synthetic methodology. This synthesis of nucleic acids is well known in the art. See. e.g., E. L. Brown, R. Belagaje, M. J. Ryan, and H. G. Khorana, *Methods in Enzymology,* 68:109–151 (1979). The DNA segments corresponding to the receptor gene are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. [See e.g., M. J. Gait, ed., *Oligonucleotide Synthesis, A Practical Approach,* (1984).j The synthetic human glutamate mGluR2 receptor gene may be designed to possess restriction endonuclease cleavage sites at either end of the transcript to facilitate isolation from and integration into expression and amplification plasmids. The choice of restriction sites are chosen so as to properly orient the coding sequence of the receptor with control sequences to achieve proper in-frame reading and expression of the mGluR2 receptor molecule. A variety of other such cleavage sites may be incorporated depending on the particular plasmid constructs employed and may be generated by techniques well known in the art.

In an alternative methodology, the desired DNA sequences can be generated using the polymerase chain reaction as described in U.S. Pat. No. 4,889,818, which is herein incorporated by reference.

In addition to the deoxyribonucleic acid of SEQ ID NO:1, this invention also provides ribonucleic acids (RNA) which comprise the RNA sequence

```
AUGGGAUCGC UGCUUGCGCU CCUGGCACUG CUGCCGCUGU GGGGUGCUGU    50

GGCUGAGGGC CCAGCCAAGA AGGUGCUGAC CCUGGAGGGA GACUUGGUGC   100

UGGGUGGGCU GUUCCCAGUG CACCAGAAGG GCGGCCCAGC AGAGGACUGU   150

GGUCCUGUCA AUGAGCACCG UGGCAUCCAG CGCCUGGAGG CCAUGCUUUU   200

UGCACUGGAC CGCAUCAACC GUGACCCGCA CCUGCUGCCU GGCGUGCGCC   250

UGGGUGCACA CAUCCUCGAC AGUUGCUCCA AGGACACACA UGCGCUGGAG   300

CAGGCACUGG ACUUUGUGCG UGCCUCACUC AGCCGUGGUG CUGAUGGCUC   350
```

-continued

```
ACGCCACAUC UGCCCCGACG GCUCUUAUGC GACCCAUGGU GAUGCUCCCA    400

CUGCCAUCAC UGGUGUUAUU GGCGGUUCCU ACAGUGAUGU CUCCAUCCAG    450

GUGGCCAACC UCUUGAGGCU AUUUCAGAUC CCACAGAUUA GCUACGCCUC    500

UACCAGUGCC AAGCUGAGUG ACAAGUCCCG CUAUGACUAC UUUGCCCGCA    550

CAGUGCCUCC UGACUUCUUC CAAGCCAAGG CCAUGGCUGA GAUUCUCCGC    600

UUCUUCAACU GGACCUAUGU GUCCACUGUG GCGUCUGAGG GCGACUAUGG    650

CGAGACAGGC AUUGAGGCCU UUGAGCUAGA GGCUCGUGCC CGCAACAUCU    700

GUGUGGCCAC CUCGGAGAAA GUGGGCCGUG CCAUGAGCCG CGCGGCCUUU    750

GAGGGUGUGG UGCGAGCCCU GCUGCAGAAG CCCAGUGCCC GCGUGGCUGU    800

CCUGUUCACC CGUUCUGAGG AUGCCCGGGA GCUGCUUGCU GCCAGCCAGC    850

GCCUCAAUGC CAGCUUCACC UGGGUGGCCA GUGAUGGUUG GGGGGCCCUG    900

GAGAGUGUGG UGGCAGGCAG UGAGGGGGCU GCUGAGGGUG CUAUCACCAU    950

CGAGCUGGCC UCCUACCCCA UCAGUGACUU UGCCUCCUAC UUCCAGAGCC   1000

UGGACCCUUG GAACAACAGC CGGAACCCCU GGUUCCGUGA AUUCUGGGAG   1050

CAGAGGUUCC GCUGCAGCUU CCGGCAGCGA GACUGCGCAG CCCACUCUCU   1100

CCGGGCUGUG CCCUUUGAGC AGGAGUCCAA GAUCAUGUUU GUGGUCAAUG   1150

CAGUGUACGC CAUGGCCCAU GCGCUCCACA ACAUGCACCG UGCCCUCUGC   1200

CCCAACACCA CCCGGCUCUG UGACGCGAUG CGGCCAGUUA ACGGGCGCCG   1250

CCUCUACAAG GACUUUGUGC UCAACGUCAA GUUUGAUGCC CCCUUUCGCC   1300

CAGCUGACAC CCACAAUGAG GUCCGCUUUG ACCGCUUUGG UGAUGGUAUU   1350

GGCCGCUACA ACAUCUUCAC CUAUCUGCGU GCAGGCAGUG GGCGCUAUCG   1400

CUACCAGAAG GUGGGCUACU GGGCAGAAGG CUUGACUCUG GACACCAGCC   1450

UCAUCCCAUG GGCCUCACCC UCAGCCGGCC CCCUGCCCGC CUCUCGCUGC   1500

AGUGAGCCCU GCCUCCAGAA UGAGGUGAAG AGUGUGCAGC CGGGCGAAGU   1550

CUGCUGCUGG CUCUGCAUUC CGUGCCAGCC CUAUGAGUAC CGAUUGGACG   1600

AAUUCACUUG CGCUGAUUGU GGCCUGGGCU ACUGGCCCAA UGCCAGCCUG   1650

ACUGGCUGCU UCGAACUGCC CCAGGAGUAC AUCCGCUGGG GCGAUGCCUG   1700

GGCUGUGGGA CCUGUCACCA UCGCCUGCCU CGGUGCCCUG GCCACCCUCU   1750

UUGUGCUGGG UGUCUUUGUG CGGCACAAUG CCACACCAGU GGUCAAGGCC   1800

UCAGGUCGGG AGCUCUGCUA CAUCCUGCUG GGUGGUGUCU UCCUCUGCUA   1850

CUGCAUGACC UUCAUCUUCA UUGCCAAGCC AUCCACGGGA GUGUGUGCCU   1900

UACGGCGUCU UGGGGUGGGC ACUGCCUUCU CUGUCUGCUA CUCAGCCCUG   1950

CUCACCAAGA CCAACCGCAU UGCACGCAUC UUCGGUGGGG CCCGGGAGGG   2000

UGCCCAGCGG CCACGCUUCA UCAGUCCUGC CUCACAGGUG GCCAUCUGCC   2050

UGGCACUUAU CUCGGGCCAG CUGCUCAUCG UGGUCGCCUG GCUGGUGGUG   2100

GAGGCACCGG GCACAGGCAA GGAGACAGCC CCCGAACGGC GGGAGGUGGU   2150

GACACUGCGC UGCAACCACC GCGAUGCAAG UAUGUUGGGC UCGCUGGCCU   2200

ACAAUGUGCU CCUCAUCGCG CUCUGCACGC UUUAUGCCUU CAAGACUCGC   2250

AAGUGCCCCG AAAACUUCAA CGAGGCCAAG UUCAUUGGCU UCACCAUGUA   2300

CACCACCUGC AUCAUCUGGC UGGCAUUCUU GCCCAUCUUC UAUGUCACCU   2350
```

-continued

```
CCAGUGACUA CCGGGUACAG ACCACCACCA UGUGCGUGUC AGUCAGCCUC    2400

AGCGGCUCCG UGGUGCUUGG CUGCCUCUUU GCGCCCAAGC UGCACAUCAU    2450

CCUCUUCCAG CCGCAGAAGA ACGUGGUUAG CCACCGGGCA CCCACCAGCC    2500

GCUUUGGCAG UGCUGCUGCC AGGGCCAGCU CCAGCCUUGG CCAAGGGUCU    2550

GGCUCCCAGU UUGUCCCCAC UGUUUGCAAU GGCCGUGAGG UGGUGGACUC    2600

GACAACGUCA UCGCUUUGA                                     2619
``` hereinafter referred to as SEQ ID NO:3, or the complementary ribonucleic acid, or a fragment of either SEQ ID NO:3 or the complement thereof. The ribonucleic acids of the present invention may be prepared using the polynucleotide synthetic methods discussed supra or they may be prepared enzymatically using RNA polymerases to transcribe a DNA template. complement thereof.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the message to be read. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to human genomic DNA or messenger RNA encoding a human glutamate receptor, is provided. Preferably, the 18 or more base pair compound is DNA.

The term "selectively hybridize" as used herein may refer to either of two situations. In the first such embodiment of this invention, the nucleic acid compounds described supra hybridize to a human glutamate receptor under more stringent hybridization conditions than these same nucleic acid compounds would hybridize to an analogous glutamate receptor of another species, e.g. murine or primate. In the second such embodiment of this invention, these probes hybridize to the mGluR2 receptor under more stringent hybridization conditions than other related compounds, including nucleic acid sequences encoding other glutamate receptors.

These probes and primers can be prepared enzymatically as described supra. In a most preferred embodiment these probes and primers are synthesized using chemical means as described sutra. Probes and primers of defined structure may also be purchased commercially.

This invention also encompasses recombinant DNA cloning vectors and expression vectors comprising the nucleic acids of the present Invention. Many of the vectors encompassed within this invention are described above. The preferred nucleic acid vectors are those which are DNA. The most preferred recombinant DNA vector comprises the isolated DNA sequence SEQ ID NO:1. Plasmid pRS133, which has been deposited with the NRRL and is available under accession number NRRL B-21174, is an especially preferred DNA vector of the present invention.

The sequence of SEQ ID NO:1 was prepared from a human fetal brain cDNA library (commercially available from Stratagene, Inc.). An aliquot of this library was used as a template with short synthetic oligonucleotide primers, designed by evaluation of the DNA sequences of the rat metabotropic receptors described in Tanabe, et al., Neuron, 8:169–172 (1992). Use of these oligonucleotides with the polymerase chain reaction generated a 1.5 kb DNA fragment, which was gel purified, radioactively labeled by PCR and used as a probe to screen the cDNA library for individual human mGluR2 clones. Using standard plaque hybridization techniques (moderate stringency, 1 M $Na^+$, 60° C.) a number of positive clones were isolated. By further dilution and hybridization, a phage clone was purified which contained the complete human mGluR2 sequence on a 2.8 kb DNA insert. A plasmid containing the insert was excised from the phage using helper phage and protocols supplied by the manufacturer. The cDNA fragment was removed from this plasmid on a 2.8 kb XbaI and BglII fragment.

Figure 2:
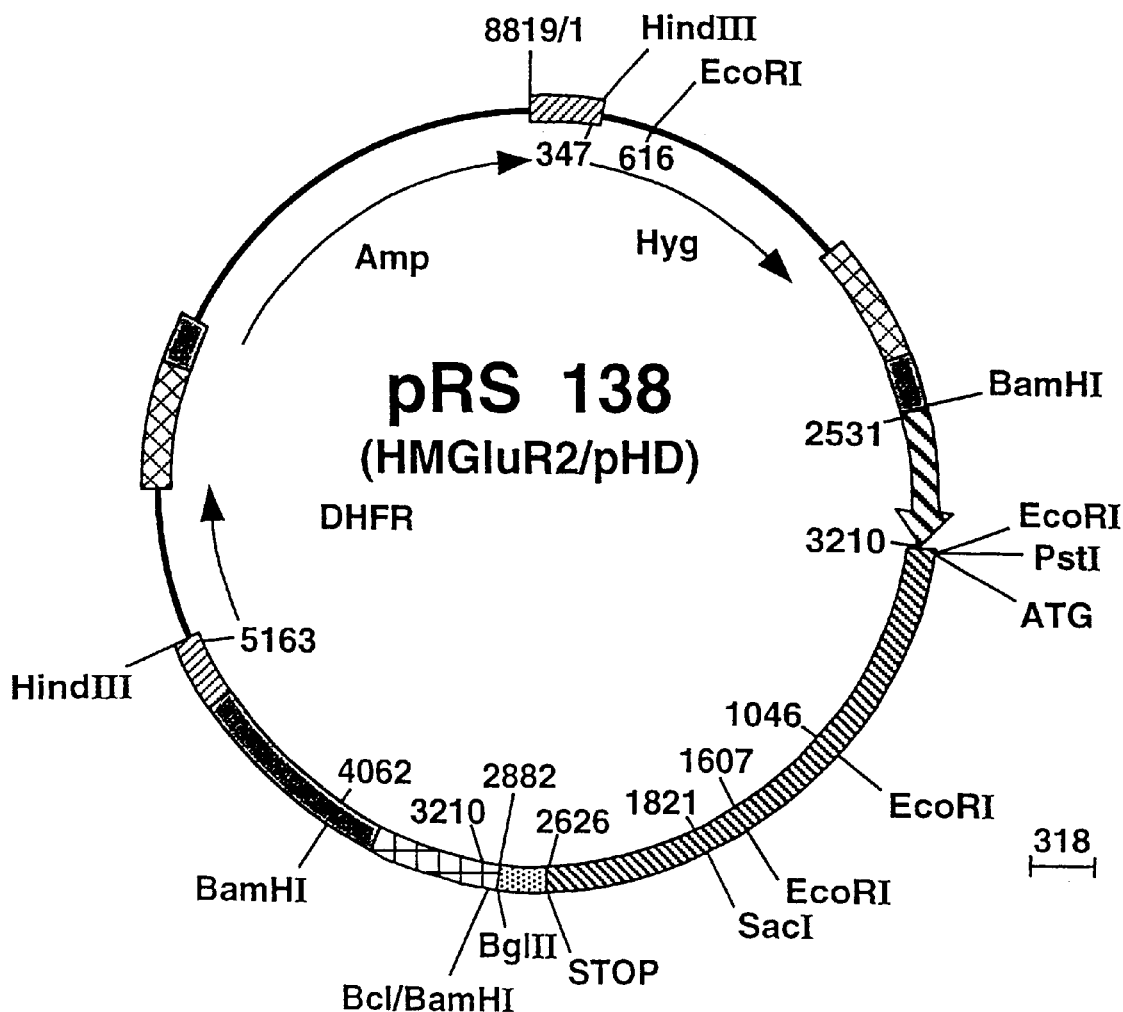
FIG. 2 is a restriction and function map of the plasmid pRS138. The arc having the wider line indicates that portion of the plasmid which corresponds to SEQ ha NO:1, infra. The arrow delineates that region of the insert which encodes the protein of SEQ ID NO:2 with the direction of the arrow indicating the natural order of transcription from the 5' end to the 3' end. The designation "EP" refers to the SV40 early promoter. "Enh" refers to the BK enhancer in tandem with the adenovirus late promoter. "Poly A" refers to the SV40 polyadenylation site. The term "3' splice" refers to the 3 splice site derived from SV40. The designation "ori" refers to a pBR322-derived origin of replication. The designation "amp$^r$" refers to the gene encoding ampicillin resistance. The designation "hyg" refers to the gene encoding hygromycin resistance.

The 2.8 kb fragment obtained was first subcloned into plasmid pSL301 (generating pRS133, as despicted in FIG. 1) in order to allow its subsequent removal on a BmHI fragment. This fragment was then inserted into the BclI site of the mammalian expression vector phd, yielding the plasmid pRS138 (FIG. 2).

The skilled artisan understands that the type of cloning vector or expression vector employed depends upon the availability of appropriate restriction sites, the type of host cell in which the vector is to be transfected or transformed, the purpose of the transfection or transformation (e.g., transient expression in an oocyte system, stable transformation as an extrachromosomal element, or integration into the host chromosome), the presence or absence of readily assayable markers (e.g., antibiotic resistance markers, metabolic markers, or the like), and the number of copies of the gene to be present in the cell.

The type of vector employed to carry the nucleic acids of the present invention may be RNA viruses, DNA viruses, lytic bacteriophages, lysogenic bacteriophages, stable bacteriophages, plasmids, viroids, and the like. The most preferred vectors of the present invention are those derived from plasmids.

When preparing an expression vector the skilled artisan understands that there are many variables to be considered. One such example is the use of a constitutive promoter, i.e. a promoter which is functional at all times, instead of a regulatable promoter which may be activated or inactivated by the artisan using heat, addition or removal of a nutrient, addition of an antibiotic, and the like. The practitioner also understands that the amount of nucleic acid or protein to be produced dictates, in part, the selection of the expression system. For experiments examining the amount of the protein expressed on the cell membrane or for experiments examining the biological function of an expressed membrane protein, for example, it may be unwise to employ an expression system which produces too much of the protein.

The addition or subtraction of certain sequences, such as a signal sequence preceding the coding sequence, may be employed by the practitioner to influence localization of the resulting polypeptide. Such sequences added to or removed from the nucleic acid compounds of the present invention are encompassed within this invention.

Plasmid pRS133 may be isolated from the deposited *E. coli* containing these plasmids using standard procedures such as cesium chloride DNA isolation. Cleaving of pRS133 with the restriction enzyme BamHI yields a four kilobase-pair fragment comprising SEQ ID NO:2. The relative locations of these restriction sites and the direction of translation of the proteins of the instant invention are depicted in FIGS. 1 and 2.

The plasmid pRS133 is readily modified to construct expression vectors that produce mGluR2 receptors in a variety of organisms, including, for example, *E. coli*, Sf9 (as host for baculovirus), Soodoptera and Saccharomyces. The current literature contains techniques for constructing AV12 expression vectors and for transforming AV12 host cells. U.S. Pat. No. 4,992,373, herein incorporated by reference, is one of many references describing these techniques.

One of the most widely employed techniques for altering a nucleic acid sequence is by way of oligonucleotide-directed site-specific mutagenesis. B. Comack, "¹Current Protocols in Molecular Biology", 8.01–8.5.9, (F. Ausubel, et al., eds. 1991). In this technique an oligonucleotide, whose sequence contains the mutation of interest, is synthesized as described supra. This oligonucleotide is then hybridized to a template containing the wild-type sequence. In a most preferred embodiment of this technique, the template is a single-stranded template. Particularly preferred are plasmids which contain regions such as the f1 intergenic region. This region allows the generation of single-stranded templates when a helper phage is added to the culture harboring the "phagemid".

After the annealing of the oligonucleotide to the template, a DNA-dependent DNA polymerase is then used to synthesize the second strand from the oliognucleotide, complementary to the template DNA. The resulting product is a heteroduplex molecule containing a mismatch due to the mutation in the oligonucleotide. After DNA replication by the host cell a mixture of two types of plasmid are present, the wild-type and the newly constructed mutant. This technique permits the introduction of convenient restriction sites such that the coding sequence may be placed immediately adjacent to whichever transcriptional or translational regulatory elements are employed by the practitioner.

The construction protocols utilized for *E. coli* can be followed to construct analogous vectors for other organisms, merely by substituting, if necessary, the appropriate regulatory elements using techniques well known to skilled artisans.

Host cells which harbor the nucleic acids provided by the present invention are also provided. A preferred host cell is an Xenopus sp. oocyte which has been injected with RNA or DNA compounds of the present invention. Most preferred oocytes of the present invention are those which harbor a sense mRNA of the present invention. Other preferred host cells include AV12 and *E. coli* cells which have been transfected and/or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is AV12. The preferred vector for expression is one which comprises SEQ ID NO:1. Another preferred host cell for this method is *E. coli*. An especially preferred expression vector in *E. coli* is one which comprises SEQ ID NO:1. Transformed host cells may be cultured under conditions well known to skilled artisans such that SEQ ID NO:2 is expressed, thereby producing mGluR2 in the recombinant host cell.

The ability of glutamate to bind to the mGluR2 receptor is essential in the development of a multitude of indications. In developing agents which act as antagonists or agonists of the mGluR2 receptor, it would be desirable, therefore, to determine those agents which bind the mGluR2 receptor. Generally, such an assay includes a method for determining whether a substance is a functional ligand of the mGluR2 receptor, said method comprising contacting a functional compound of the mGluR2 receptor with said substance, monitoring binding activity by physically detectable means, and identifying those substances which effect a chosen response. Preferably, the physically detectable means as competition with labeled glutamate or binding of ligand in an cocyte transient expression system The instant invention provides such a screening system useful for discovering agents which compete with glutamate for binding to the mGluR2 receptor, said screening system comprising the steps of:

a) isolating a human mGluR2 receptor;

b) exposing said human mGluR2 receptor to a potential inhibitor or surrogate of the glutamate/mGluR2 receptor complex;

c) introducing glutamate;

d) removing non-specifically bound molecules; and e) quantifying the concentration of bound potential inhibitor and/or glutamate.

This allows one to rapidly screen for inhibitors or surrogates of the formation of the glutamate/mGluR2 receptor complex. Utilization of the screening system described above provides a sensitive and rapid means to determine compounds which interfere with the formation of the glutamate/mGluR2 receptor complex. This screening system may also be adapted to automated procedures such as a PANDEX® (Baxter-Dade Diagnostics) system allowing for efficient high-volume screening of potential therapeutic agents.

In such a screening protocol a mGluR2 receptor is prepared as elsewhere described herein, preferably using recombinant DNA technology. A sample of a test compound is then introduced to the reaction vessel containing the mGluR2 receptor followed by the addition of glutamate. In the alternative the glutamate may be added simultaneously with the test compound. Unbound molecules are washed free and the eluent inspected for the presence of glutamate or the test compound.

For example, in a preferred method of the invention, radioactively or chemically labeled glutamate may be used. The eluent is then scored for the chemical label or radioactivity. The absence or diminution of the chemical label or radioactivity indicates the formation of the glutamate/mGluR2 receptor complex. This indicates that the test compound has not effectively competed with glutamate in the formation of the glutamate/mGluR2 receptor complex. The presence of the chemical label or radioactivity indicates that the test compound has competed with glutamate in the formation of the glutamate/mGluR2 receptor complex. Similarly, a radioactively or chemically labeled test compound may be used in which case the same steps as outlined above would be used except that the interpretation of results would be the converse of using radioactively or chemically labelled glutamate.

As would be understood by the skilled artisan these assays may also be performed such that the practitioner measures the radioactivity or fluorescence remaining with the protein, not in the eluent. A preferred such assay employs radiolabeled glutamate. After the competition reaction has been performed the reaction mixture is then passed through a filter, the filter retaining the receptor and whatever is complexed with the receptor. The radioactivity on each filter is then measured in a scintillation counter. In such an assay higher amounts of radiolabel present indicate lower affinity for the receptor by the test compound.

The mGluR2 receptor may be free in solution or bound to a solid support. Whether the mGluR2 receptor is bound to a support or is free in solution, it is generally important that the conformation of the protein be conserved. In a preferred practice of the invention, therefore, the mGluR2 receptor is suspended in a hydrophobic environment employing natural or synthetic detergents, membrane suspensions, and the like. Preferred detergent complexes include the zwitterionic detergent 3-((3-cholamidopropyl)-dimethylammonio]-1-propane sulfonate ("CHAPS") as well as sodium deoxycholate.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom Indicate high affinity or low affinity to mGluR2 receptor, because skilled artisans will recognize that any information regarding binding or selectivity of a particular compound is beneficial in the pharmaceutical development of drugs.

In one such competition assay, a battery of known glutamate receptor antagonists, agonists, and partial agonists are evaluated for their relative abilities to inhibit the binding of [$^3$H]glutamate to the human mGluR2 receptor of the present invention.

In this assay suspension cells stably expressing the cloned human mGluR2 receptor are harvested by centrifugation at 2200× g for 15 minutes at 4° C. Membranes for the binding assays are prepared by vortexing the cell pellet in 50 mM Tris-HCl, pH 7.4 (0.5×10$^9$ cells/30 ml). The tissue suspension is then centrifuged at 39,800× g for 10 minutes at 4° C. This procedure is repeated for a total of three washes, with a 10 minute incubation at 37° C. between the second and third washes. The final pellet is homogenized in 67 mM Tris.HCl, pH 7.4, at 12.5–10$^6$ cells/ml using a Tissumizer® (Tekmar, Cincinati, Ohio) at setting 65 for 15 seconds.

Binding assays are performed in triplicate in 0.8 ml total volume. Volumes of 200 l of membrane suspension (0.07–0.10 mg of protein) and 200 Al of drug dilution in water are added to 400 $\mu$l of 67 mM of Tris-HCl, pH 7.4, containing [$^3$H]glutamate (35 nM final concentration, 23.7 Ci/mole), calcium chloride (3 mM), pargyline (10 $\mu$M), and L-ascorbic acid (5.7 nM). The reaction mixtures are incubated at 37° C. for 15 minutes and then rapidly filtered, using a Brandel™ cell harvester (Model MB-48R; Brandel, Gaithersburg, Maryland) over Whatman GF/B filters that had been presoaked in 0.5% polyethyleneimine and precooled with ice-cold 50 mM Tris.HCl, pH 7.4. The filters are then washed rapidly times with ice-cold (4×1 ml each).

The amount of [$^3$H]glutamate trapped on the filters is determined by liquid scintillation counting. For the competition experiments, six concentrations of displacing drugs are used, ranging from 10$^5$ to 10$^{10}$ M. The IC$_{50}$ values are determined by nonlinear regression analysis (Systat™; Systat Inc., Evanston, Ill.) which may be converted to $K_i$ values using the Cheng-Prusoff equation. Y. Cheng and W. H. Prusoff, *Biochemical Pharmacology*, 22:3099–3108 (1973).

In this particular type of competition assay the following compounds are frequently used.

(a) Quisqualate—a compound of the formula

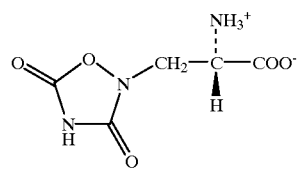

having the chemical name (S)-α-amino-3,5-dioxo-1,2,4-oxadiazolidine-2-propanoate. This compound can be prepared as described in J. E. Baldwin, et al., *Chemical Communications*, 256 (1985).

(b) Glutamate—a compound of the formula

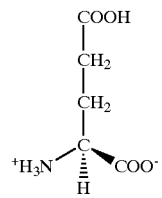

having the chemical name 1-aminopropane-1,3-dicarboxylic acid. This compound is readily available and can be purchased commercially from several sources.

(c) Ibotenate—a compound of the formula

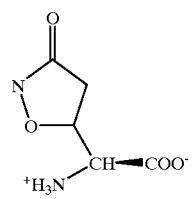

having the chemical name α-amino-3-hydroxy-5-isoxazoleacetate, which can be prepared as described in U.S. Pat. No. 3,459,862, herein incorporated by reference.

(d) t-ACPD—a compound of the formula

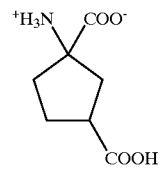

having the chemical name 1-aminocyclopentane-1,3-dicarboxylic acid. This compound can be purchased commercially from several sources.

(e) (2R,4R) 4-amino-pyrrolidine-2,4-dicarboxylic acid, a compound of the formula

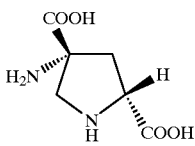

which is described in co-pending U.S. patent application Ser. No. 08/295,337, filed Aug. 24, 1994. Many 1-substituted derivatives of this dicarboxylic acid are also effective as mGluR2 antagonists.

The previously described screening system identifies compounds which competitively bind to the mGluR2 receptor. Determination of the ability of such compounds to stimulate or inhibit the action of the mGluR2 receptor is essential to further development of such compounds for therapeutic applications. The need for a bioactivity assay system which determines the response of the mGluR2 receptor to a compound is clear. The instant invention provides such a bioactivity assay, said assay comprising the steps of:

a) transfecting a mammalian host cell with an expression vector comprising DNA encoding a mGluR2 receptor;

b) culturing said host cell under conditions such that the DNA encoding the mGluR2 receptor is expressed, c) exposing said host cell so transfected to a test compound, and d) measuring the change in a physiological condition known to be influenced by the binding of glutamate to the mGluR2 receptor relative to a control in which the transfected host cell is exposed to glutamate.

An oocyte transient expression system can be constructed according to the procedure described in S. Lübbert, et al., *Proceedings of the National Academy of Sciences (USA)*, 84:4332 (1987).

In an especially preferred embodiment of this invention an assay measuring the inhibition of forskolin-stimulatedcAMP synthesis was performed. The inhibition of cAMP synthesis is known to positively correlated with the addition of glutamate to cells containing certain types of metabotropic receptors.

Adenylate Cyclase Activity.

Adenylate cyclase activity was determined in initial experiments in transfected mammalian cells, using standard techniques. See, e.g, N. Adham, et al., supra,; R. L. Weinshank, et al., *Proceedings of the National Academy of Sciences (USA)*, 89:3630–3634 (1992), and the references cited therein.

Mammalian cells (the cell line AV12-664 was employed here) are stably transfected with the plasmid pRS138, containing human mGluR2 cDNA inserted in the plasmid vector pHD, as depicted in FIG. 2. The cells are maintained in a medium consisting of Dulbecco's Modified Eagle's Medium (DMEM) containing 5% dialyzed fetal calf serum, 10 mM HEPES buffer (pH 7.3), 1 mM sodium pyruvate, 1 mM glutamine, and 200 µg/ml hygromycin.

For the assay the cells are disassociated from stock culture flasks with trypsin, and planted in 24-well plastic culture dishes (15 mm wells) at a density of 500–700,000 cells per well using the same culture medium. After twenty four hours incubation in a humidified carbon dioxide incubator, the cell monolayers are washed with buffer (Dulbecco's phosphate-buffered saline containing 0.5 mM isobutylmethylxanthine and 3 mM glucose) and then incubated in the same buffer at 37° C. for 30 minutes. The monolayers are then washed four additional times with buffer.

Drugs and forskolin, or forskolin alone, dissolved in buffer, are added after the final wash. After incubating for 20 minutes at 37° C., 0.5 ml of 8 mM EDTA is added to each well. The plates are then placed in a boiling water bath for about four minutes. The supernatant fluids are then recovered from the wells and lyophilized. Cyclic adenosinemono-phosphate determinations are carried out on the lyophilized samples using commercially available radioimmunoassay kits, following the manufacturer's instructions. The cAMP level in wells containing drug are the compared to the forskolin controls.

In another embodiment this invention provides a method for identifying, in a test sample, DNA homologous to a probe of the present invention, wherein the test nucleic acid is contacted with the probe under hybridizing conditions and identified as being homologous to the probe. Hybridization techniques are well known in the art. See, e J. Sambrook, et al., supra, at Chapter 11.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. See. e.g. J. Sambrook, supra. Such procedures may be employed in searching for persons with mutations in these receptors by the well-known techniques of restriction fragment length polymorphisms (RFLP), the procedures of which are described in U.S. Pat. No. 4,666,828, issued May 19, 1987, the entire contents of which is herein incorporated by reference.

The proteins of this invention as well as fragments of these proteins may be used as antigens for the synthesis of antibodies. The term "antibody" as used herein describes antibodies, fragments of antibodies (such as, but not limited, to Fab, Fab', Fab$_2$', and Fv fragments), and chimeric, humanized, veneered, resurfaced, or CDR-grafted antibodies capable of binding antigens of a similar nature as the parent antibody molecule from which they are derived. The instant invention also encompasses single chain polypeptide binding molecules.

The term "antibody" as used herein is not limited by the manner in which the antibodies are produced, whether such production is in situ or not. The term "antibody" as used in this specification encompasses those antibodies produced by recombinant DNA technology means including, but not limited, to expression in bacteria, yeast, insect cell lines, or mammalian cell lines.

The production of antibodies, both monoclonal and polyclonal, in animals, especially mice, is well known in the art. See. e.g., C. Milstein, *Handbook of Experimental Immunology*, (Blackwell Scientific Pub., 1986); J. Goding, *Monoclonal Antibodies: Principles and Practice*, (Academic Press, 1983). For the production of monoclonal antibodies the basic process begins with injecting a mouse, or other suitable animal, with an immunogen. The mouse is subsequently sacrificed and cells taken from its spleen are fused with myeloma cells, resulting in a hybridoma that reproduces in vitro. The population of hybridomas is screened to isolate individual clones, each of which secretes a single antibody species, specific for the immunogen. The individual antibody species obtained in this way is each the product of a single B cell from the immune animal generated in response to a specific antigenic site, or epitope, recognized on the immunogenic substance.

Chimeric antibodies are described in U.S. Pat. No. 4,816,567, which issued Mar. 28, 1989 to S. Cabilly, e al. This reference discloses methods and vectors for the preparation of chimeric antibodies. The entire contents of U.S. Pat. No. 4,816,567 are herein incorporated by reference. An alternative approach to production of genetically engineered antibodies is provided in U.S. Pat. No. 4,816,397, which also issued Mar. 28, 1989 to M. Boss, et al., the entire contents of which are herein incorporated by reference. The Boss patent teaches the simultaneous co-expression of the heavy and light chains of the antibody in the same host cell.

The approach of U.S. Pat. No. 4,816,397 has been further refined as taught in European Patent Publication No. 0 239 400, which published Sep. 30, 1987. The teachings of this European patent publication (Winter) are a preferred format for the genetic engineering of the reactive monoclonal antibodies of this invention. The Winter technology involves the replacement of complementarity determining regions (CDRs) of a human antibody with the CDRs of a murine monoclonal antibody thereby converting the specificity of the human antibody to the specificity of the murine antibody which was the source of the CDR regions. This "CDR grafting" technology affords a molecule containing minimal murine sequence and thus is less immunogenic.

Single chain antibody technology is yet another variety of genetically engineered antibody which is now well known in the art. See, e.g. R. E. Bird, et al., *Science 242:423–426* (1988); PCT Publication No. WO 88/01649, which was published Mar. 10, 1988. The single chain antibody technology involves joining the binding regions of heavy and light chains with a polypeptide sequence to generate a single polypeptide having the binding specificity of the antibody from which it was derived.

The aforementioned genetic engineering approaches provide the skilled artisan with numerous means to generate molecules which retain the binding characteristics of the parental antibody while affording a less immunogenic format.

These antibodies are used in diagnostics, therapeutics or in diagnostic/therapeutic combinations. By "diagnostics" as used herein is meant testing that is related to either the in vitro or in vivo diagnosis of disease states or biological status in mammals, preferably in humans. By "therapeutics" and "therapeutic/diagnostic combinations" as used herein is respectively meant the treatment or the diagnosis and treatment of disease states or biological status by the in vivo administration to mammals, preferably humans, of the antibodies of the present invention. The antibodies of the present invention are especially preferred in the diagnosis and/or treatment of conditions associated with an excess or deficiency of mGluR2 receptors.

In addition to being functional as direct therapeutic and diagnostic aids, the availability of a family of antibodies which are specific for the mGluR2 receptor enables the development of numerous assay systems for detecting agents which bind to this receptor. One such assay system comprises radiolabeling mGluR2 receptor-specific antibodies with a radionuclide such as $^{125}$I and measuring displacement of the radiolabeled mGluR2 receptor-specific antibody from solid phase mGluR2 receptor in the presence of a potential antagonist.

Numerous other assay systems are also readily adaptable to detect agents which bind mGluR2 receptor. Examples of these aforementioned assay systems are discussed in *Methods in Enzymology,* (J. Langone. and H. Vunakis, eds. 1981), Vol. 73, Part B, the contents of which are herein incorporated by reference. Skilled artisans are directed to Section II of *Methods in Enzymology,* Vol. 73, Part B, supra, which discusses labeling of antibodies and antigens, and Section IV, which discusses immunoassay methods.

In addition to the aforementioned antibodies specific for the mGluR2 receptor, this invention also provides antibodies which are specific for the hypervariable regions of the anti-mGluR2 receptor antibodies. Some such anti-idiotypic antibodies would resemble the original epitope, the mGluR2 receptor, and, therefore, would be useful in evaluating the effectiveness of compounds which are potential antagonists, agonists, or partial agonists of the mGluR2 receptor. See. e.g., Cleveland, et al., *Nature (London),* 305:56 (1983); Wasserman, et al., *Proceedings of the National Academy of Sciences (USA),* 79:4810 (1982).

In another embodiment, this invention encompasses pharmaceutical formulations for parenteral administration which contain, as the active ingredient, the anti-mGluR2 receptor antibodies described, supra. Such formulations are prepared by methods commonly used in pharmaceutical chemistry.

Products for parenteral administration are often formulated and distributed in solid, preferably freeze-dried form, for reconstitution immediately before use. Such formulations are useful compositions of the present invention. Their preparation is well understood by pharmaceutical chemists.

In general, these formulations comprise the active ingredient in combination with a mixture of inorganic salts, to confer isotonicity, as well as dispersing agents such as lactose, to allow the dried preparation to dissolve quickly upon reconstitution. Such formulations are reconstituted for use with highly purified water to a known concentration.

Alternatively, a water soluble form of the antibody can be dissolved in one of the commonly used intravenous fluids and administered by infusion. Such fluids include physiological saline, Ringer's solution or a 5% dextrose solution.

We claim:

1. A method of evaluating the effectiveness of a test compound for the treatment or prevention of a condition associated with a deficiency of stimulation of a human mGluR2 receptor which method comprises:
   a) introducing into a mammalian host cell an expression vector comprising DNA encoding a human mGluR2 receptor, wherein said receptor comprises SEQ ID NO:2;
   b) culturing said host cell under conditions such that the human mGluR2 receptor is expressed;
   c) exposing said host cell expressing the human mGluR2 receptor to a test compound; and
   d) measuring the change in a physiological condition known to be influenced by the binding of native ligand to the human mGluR2 receptor relative to a control in which the transfected host cell is exposed to native ligand.

2. A method of evaluating the effectiveness of a test compound for the treatment or prevention of a condition associated with an excess of stimulation of a human mGluR2 receptor compounds which method comprises:
   a) introducing into a mammalian host cell an expression vector comprising DNA encoding a human mGluR2 receptor wherein said receptor comprises SEQ ID NO:2;
   b) culturing said host cell under conditions such that the human mGluR2 receptor is expressed;
   c) exposing said host cell expressing the human mGluR2 receptor to a test compound;
   d) exposing said host cell expressing the mGluR2 receptor to glutamate simultaneously with or following the exposure to the test compound; and
   e) measuring the change in a physiological condition known to be influenced by the binding of glutamate to the human mGluR2 receptor relative to a control in which the transfected host cell is exposed to only glutamate.

3. A method of evaluating the effectiveness of a test compound for use in the treatment or prevention of conditions associated with an excess or deficiency of stimulation of a human mGluR2 receptor comprising the steps of:
   f) isolating a human mGluR2 receptor comprising the amino acid sequence given by SEQ ID NO:2;
   f) exposing said isolated human mGluR2 receptor to the test compound;
   f) exposing the isolated human mGluR2 receptor to glutamate simultaneously with or following the introduction of the test compound;
   f) removing non-specifically bound glutamate or test compound;
   f) quantifying the concentration of test compound or glutamate bound to the human mGluR2 receptor; and
   f) comparing the concentration of test compound or glutamate bound to the human mGluR2 receptor to a control in which no test compound were added.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 2619 base pairs
        (B) TYPE: nucleic acid
        (C) STRANDEDNESS: single
        (D) TOPOLOGY: linear (ii) MOLECULE TYPE: cDNA -continued

```
    (ix) FEATURE:
          (A) NAME/KEY: CDS
          (B) LOCATION: 1..2616

(xi) SEQUENCE DESCRIPTION: SEQ ID NO:1:

ATG GGA TCG CTG CTT GCG CTC CTG GCA CTG CTG CCG CTG TGG GGT GCT        48
Met Gly Ser Leu Leu Ala Leu Leu Ala Leu Leu Pro Leu Trp Gly Ala
 1               5                  10                  15

GTG GCT GAG GGC CCA GCC AAG AAG GTG CTG ACC CTG GAG GGA GAC TTG        96
Val Ala Glu Gly Pro Ala Lys Lys Val Leu Thr Leu Glu Gly Asp Leu
            20                  25                  30

GTG CTG GGT GGG CTG TTC CCA GTG CAC CAG AAG GGC GGC CCA GCA GAG       144
Val Leu Gly Gly Leu Phe Pro Val His Gln Lys Gly Gly Pro Ala Glu
        35                  40                  45

GAC TGT GGT CCT GTC AAT GAG CAC CGT GGC ATC CAG CGC CTG GAG GCC       192
Asp Cys Gly Pro Val Asn Glu His Arg Gly Ile Gln Arg Leu Glu Ala
    50                  55                  60

ATG CTT TTT GCA CTG GAC CGC ATC AAC CGT GAC CCG CAC CTG CTG CCT       240
Met Leu Phe Ala Leu Asp Arg Ile Asn Arg Asp Pro His Leu Leu Pro
65                  70                  75                  80

GGC GTG CGC CTG GGT GCA CAC ATC CTC GAC AGT TGC TCC AAG GAC ACA       288
Gly Val Arg Leu Gly Ala His Ile Leu Asp Ser Cys Ser Lys Asp Thr
                85                  90                  95

CAT GCG CTG GAG CAG GCA CTG GAC TTT GTG CGT GCC TCA CTC AGC CGT       336
His Ala Leu Glu Gln Ala Leu Asp Phe Val Arg Ala Ser Leu Ser Arg
            100                 105                 110

GGT GCT GAT GGC TCA CGC CAC ATC TGC CCC GAC GGC TCT TAT GCG ACC       384
Gly Ala Asp Gly Ser Arg His Ile Cys Pro Asp Gly Ser Tyr Ala Thr
        115                 120                 125

CAT GGT GAT GCT CCC ACT GCC ATC ACT GGT GTT ATT GGC GGT TCC TAC       432
His Gly Asp Ala Pro Thr Ala Ile Thr Gly Val Ile Gly Gly Ser Tyr
    130                 135                 140

AGT GAT GTC TCC ATC CAG GTG GCC AAC CTC TTG AGG CTA TTT CAG ATC       480
Ser Asp Val Ser Ile Gln Val Ala Asn Leu Leu Arg Leu Phe Gln Ile
145                 150                 155                 160

CCA CAG ATT AGC TAC GCC TCT ACC AGT GCC AAG CTG AGT GAC AAG TCC       528
Pro Gln Ile Ser Tyr Ala Ser Thr Ser Ala Lys Leu Ser Asp Lys Ser
                165                 170                 175

CGC TAT GAC TAC TTT GCC CGC ACA GTG CCT CCT GAC TTC TTC CAA GCC       576
Arg Tyr Asp Tyr Phe Ala Arg Thr Val Pro Pro Asp Phe Phe Gln Ala
            180                 185                 190

AAG GCC ATG GCT GAG ATT CTC CGC TTC TTC AAC TGG ACC TAT GTG TCC       624
Lys Ala Met Ala Glu Ile Leu Arg Phe Phe Asn Trp Thr Tyr Val Ser
        195                 200                 205

ACT GTG GCG TCT GAG GGC GAC TAT GGC GAG ACA GGC ATT GAG GCC TTT       672
Thr Val Ala Ser Glu Gly Asp Tyr Gly Glu Thr Gly Ile Glu Ala Phe
    210                 215                 220

GAG CTA GAG GCT CGT GCC CGC AAC ATC TGT GTG GCC ACC TCG GAG AAA       720
Glu Leu Glu Ala Arg Ala Arg Asn Ile Cys Val Ala Thr Ser Glu Lys
225                 230                 235                 240

GTG GGC CGT GCC ATG AGC CGC GCG GCC TTT GAG GGT GTG GTG CGA GCC       768
Val Gly Arg Ala Met Ser Arg Ala Ala Phe Glu Gly Val Val Arg Ala
                245                 250                 255

CTG CTG CAG AAG CCC AGT GCC CGC GTG GCT GTC CTG TTC ACC CGT TCT       816
Leu Leu Gln Lys Pro Ser Ala Arg Val Ala Val Leu Phe Thr Arg Ser
            260                 265                 270

GAG GAT GCC CGG GAG CTG CTT GCT GCC AGC CAG CGC CTC AAT GCC AGC       864
Glu Asp Ala Arg Glu Leu Leu Ala Ala Ser Gln Arg Leu Asn Ala Ser
        275                 280                 285
```

```
TTC ACC TGG GTG GCC AGT GAT GGT TGG GGG GCC CTG GAG AGT GTG GTG      912
Phe Thr Trp Val Ala Ser Asp Gly Trp Gly Ala Leu Glu Ser Val Val
    290                 295                 300

GCA GGC AGT GAG GGG GCT GCT GAG GGT GCT ATC ACC ATC GAG CTG GCC      960
Ala Gly Ser Glu Gly Ala Ala Glu Gly Ala Ile Thr Ile Glu Leu Ala
305                 310                 315                 320

TCC TAC CCC ATC AGT GAC TTT GCC TCC TAC TTC CAG AGC CTG GAC CCT     1008
Ser Tyr Pro Ile Ser Asp Phe Ala Ser Tyr Phe Gln Ser Leu Asp Pro
                325                 330                 335

TGG AAC AAC AGC CGG AAC CCC TGG TTC CGT GAA TTC TGG GAG CAG AGG     1056
Trp Asn Asn Ser Arg Asn Pro Trp Phe Arg Glu Phe Trp Glu Gln Arg
            340                 345                 350

TTC CGC TGC AGC TTC CGG CAG CGA GAC TGC GCA GCC CAC TCT CTC CGG     1104
Phe Arg Cys Ser Phe Arg Gln Arg Asp Cys Ala Ala His Ser Leu Arg
        355                 360                 365

GCT GTG CCC TTT GAG CAG GAG TCC AAG ATC ATG TTT GTG GTC AAT GCA     1152
Ala Val Pro Phe Glu Gln Glu Ser Lys Ile Met Phe Val Val Asn Ala
    370                 375                 380

GTG TAC GCC ATG GCC CAT GCG CTC CAC AAC ATG CAC CGT GCC CTC TGC     1200
Val Tyr Ala Met Ala His Ala Leu His Asn Met His Arg Ala Leu Cys
385                 390                 395                 400

CCC AAC ACC ACC CGG CTC TGT GAC GCG ATG CGG CCA GTT AAC GGG CGC     1248
Pro Asn Thr Thr Arg Leu Cys Asp Ala Met Arg Pro Val Asn Gly Arg
                405                 410                 415

CGC CTC TAC AAG GAC TTT GTG CTC AAC GTC AAG TTT GAT GCC CCC TTT     1296
Arg Leu Tyr Lys Asp Phe Val Leu Asn Val Lys Phe Asp Ala Pro Phe
            420                 425                 430

CGC CCA GCT GAC ACC CAC AAT GAG GTC CGC TTT GAC CGC TTT GGT GAT     1344
Arg Pro Ala Asp Thr His Asn Glu Val Arg Phe Asp Arg Phe Gly Asp
        435                 440                 445

GGT ATT GGC CGC TAC AAC ATC TTC ACC TAT CTG CGT GCA GGC AGT GGG     1392
Gly Ile Gly Arg Tyr Asn Ile Phe Thr Tyr Leu Arg Ala Gly Ser Gly
    450                 455                 460

CGC TAT CGC TAC CAG AAG GTG GGC TAC TGG GCA GAA GGC TTG ACT CTG     1440
Arg Tyr Arg Tyr Gln Lys Val Gly Tyr Trp Ala Glu Gly Leu Thr Leu
465                 470                 475                 480

GAC ACC AGC CTC ATC CCA TGG GCC TCA CCC TCA GCC GGC CCC CTG CCC     1488
Asp Thr Ser Leu Ile Pro Trp Ala Ser Pro Ser Ala Gly Pro Leu Pro
                485                 490                 495

GCC TCT CGC TGC AGT GAG CCC TGC CTC CAG AAT GAG GTG AAG AGT GTG     1536
Ala Ser Arg Cys Ser Glu Pro Cys Leu Gln Asn Glu Val Lys Ser Val
            500                 505                 510

CAG CCG GGC GAA GTC TGC TGC TGG CTC TGC ATT CCG TGC CAG CCC TAT     1584
Gln Pro Gly Glu Val Cys Cys Trp Leu Cys Ile Pro Cys Gln Pro Tyr
        515                 520                 525

GAG TAC CGA TTG GAC GAA TTC ACT TGC GCT GAT TGT GGC CTG GGC TAC     1632
Glu Tyr Arg Leu Asp Glu Phe Thr Cys Ala Asp Cys Gly Leu Gly Tyr
    530                 535                 540

TGG CCC AAT GCC AGC CTG ACT GGC TGC TTC GAA CTG CCC CAG GAG TAC     1680
Trp Pro Asn Ala Ser Leu Thr Gly Cys Phe Glu Leu Pro Gln Glu Tyr
545                 550                 555                 560

ATC CGC TGG GGC GAT GCC TGG GCT GTG GGA CCT GTC ACC ATC GCC TGC     1728
Ile Arg Trp Gly Asp Ala Trp Ala Val Gly Pro Val Thr Ile Ala Cys
                565                 570                 575

CTC GGT GCC CTG GCC ACC CTC TTT GTG CTG GGT GTC TTT GTG CGG CAC     1776
Leu Gly Ala Leu Ala Thr Leu Phe Val Leu Gly Val Phe Val Arg His
            580                 585                 590

AAT GCC ACA CCA GTG GTC AAG GCC TCA GGT CGG GAG CTC TGC TAC ATC     1824
Asn Ala Thr Pro Val Val Lys Ala Ser Gly Arg Glu Leu Cys Tyr Ile
        595                 600                 605
```

```
CTG CTG GGT GGT GTC TTC CTC TGC TAC TGC ATG ACC TTC ATC TTC ATT      1872
Leu Leu Gly Gly Val Phe Leu Cys Tyr Cys Met Thr Phe Ile Phe Ile
        610                 615                 620

GCC AAG CCA TCC ACG GGA GTG TGT GCC TTA CGG CGT CTT GGG GTG GGC      1920
Ala Lys Pro Ser Thr Gly Val Cys Ala Leu Arg Arg Leu Gly Val Gly
625                 630                 635                 640

ACT GCC TTC TCT GTC TGC TAC TCA GCC CTG CTC ACC AAG ACC AAC CGC      1968
Thr Ala Phe Ser Val Cys Tyr Ser Ala Leu Leu Thr Lys Thr Asn Arg
                    645                 650                 655

ATT GCA CGC ATC TTC GGT GGG GCC CGG GAG GGT GCC CAG CGG CCA CGC      2016
Ile Ala Arg Ile Phe Gly Gly Ala Arg Glu Gly Ala Gln Arg Pro Arg
            660                 665                 670

TTC ATC AGT CCT GCC TCA CAG GTG GCC ATC TGC CTG GCA CTT ATC TCG      2064
Phe Ile Ser Pro Ala Ser Gln Val Ala Ile Cys Leu Ala Leu Ile Ser
        675                 680                 685

GGC CAG CTG CTC ATC GTG GTC GCC TGG CTG GTG GTG GAG GCA CCG GGC      2112
Gly Gln Leu Leu Ile Val Val Ala Trp Leu Val Val Glu Ala Pro Gly
    690                 695                 700

ACA GGC AAG GAG ACA GCC CCC GAA CGG CGG GAG GTG GTG ACA CTG CGC      2160
Thr Gly Lys Glu Thr Ala Pro Glu Arg Arg Glu Val Val Thr Leu Arg
705                 710                 715                 720

TGC AAC CAC CGC GAT GCA AGT ATG TTG GGC TCG CTG GCC TAC AAT GTG      2208
Cys Asn His Arg Asp Ala Ser Met Leu Gly Ser Leu Ala Tyr Asn Val
                    725                 730                 735

CTC CTC ATC GCG CTC TGC ACG CTT TAT GCC TTC AAG ACT CGC AAG TGC      2256
Leu Leu Ile Ala Leu Cys Thr Leu Tyr Ala Phe Lys Thr Arg Lys Cys
            740                 745                 750

CCC GAA AAC TTC AAC GAG GCC AAG TTC ATT GGC TTC ACC ATG TAC ACC      2304
Pro Glu Asn Phe Asn Glu Ala Lys Phe Ile Gly Phe Thr Met Tyr Thr
        755                 760                 765

ACC TGC ATC ATC TGG CTG GCA TTC TTG CCC ATC TTC TAT GTC ACC TCC      2352
Thr Cys Ile Ile Trp Leu Ala Phe Leu Pro Ile Phe Tyr Val Thr Ser
    770                 775                 780

AGT GAC TAC CGG GTA CAG ACC ACC ACC ATG TGC GTG TCA GTC AGC CTC      2400
Ser Asp Tyr Arg Val Gln Thr Thr Thr Met Cys Val Ser Val Ser Leu
785                 790                 795                 800

AGC GGC TCC GTG GTG CTT GGC TGC CTC TTT GCG CCC AAG CTG CAC ATC      2448
Ser Gly Ser Val Val Leu Gly Cys Leu Phe Ala Pro Lys Leu His Ile
                    805                 810                 815

ATC CTC TTC CAG CCG CAG AAG AAC GTG GTT AGC CAC CGG GCA CCC ACC      2496
Ile Leu Phe Gln Pro Gln Lys Asn Val Val Ser His Arg Ala Pro Thr
            820                 825                 830

AGC CGC TTT GGC AGT GCT GCT GCC AGG GCC AGC TCC AGC CTT GGC CAA      2544
Ser Arg Phe Gly Ser Ala Ala Ala Arg Ala Ser Ser Ser Leu Gly Gln
        835                 840                 845

GGG TCT GGC TCC CAG TTT GTC CCC ACT GTT TGC AAT GGC CGT GAG GTG      2592
Gly Ser Gly Ser Gln Phe Val Pro Thr Val Cys Asn Gly Arg Glu Val
    850                 855                 860

GTG GAC TCG ACA ACG TCA TCG CTT TGA                                  2619
Val Asp Ser Thr Thr Ser Ser Leu
865                 870

(2) INFORMATION FOR SEQ ID NO:2:

(i) SEQUENCE CHARACTERISTICS:
        (A) LENGTH: 872 amino acids
        (B) TYPE: amino acid
        (D) TOPOLOGY: linear (ii) MOLECULE TYPE: protein
```

-continued (xi) SEQUENCE DESCRIPTION: SEQ ID NO:2:

```
Met Gly Ser Leu Leu Ala Leu Ala Leu Leu Pro Leu Trp Gly Ala
 1               5                  10                  15

Val Ala Glu Gly Pro Ala Lys Lys Val Leu Thr Leu Glu Gly Asp Leu
                20                  25                  30

Val Leu Gly Gly Leu Phe Pro Val His Gln Lys Gly Gly Pro Ala Glu
            35                  40                  45

Asp Cys Gly Pro Val Asn Glu His Arg Gly Ile Gln Arg Leu Glu Ala
        50                  55                  60

Met Leu Phe Ala Leu Asp Arg Ile Asn Arg Asp Pro His Leu Leu Pro
65                  70                  75                  80

Gly Val Arg Leu Gly Ala His Ile Leu Asp Ser Cys Ser Lys Asp Thr
                85                  90                  95

His Ala Leu Glu Gln Ala Leu Asp Phe Val Arg Ala Ser Leu Ser Arg
            100                 105                 110

Gly Ala Asp Gly Ser Arg His Ile Cys Pro Asp Gly Ser Tyr Ala Thr
        115                 120                 125

His Gly Asp Ala Pro Thr Ala Ile Thr Gly Val Ile Gly Gly Ser Tyr
130                 135                 140

Ser Asp Val Ser Ile Gln Val Ala Asn Leu Leu Arg Leu Phe Gln Ile
145                 150                 155                 160

Pro Gln Ile Ser Tyr Ala Ser Thr Ser Ala Lys Leu Ser Asp Lys Ser
                165                 170                 175

Arg Tyr Asp Tyr Phe Ala Arg Thr Val Pro Pro Asp Phe Phe Gln Ala
            180                 185                 190

Lys Ala Met Ala Glu Ile Leu Arg Phe Phe Asn Trp Thr Tyr Val Ser
        195                 200                 205

Thr Val Ala Ser Glu Gly Asp Tyr Gly Glu Thr Gly Ile Glu Ala Phe
210                 215                 220

Glu Leu Glu Ala Arg Ala Arg Asn Ile Cys Val Ala Thr Ser Glu Lys
225                 230                 235                 240

Val Gly Arg Ala Met Ser Arg Ala Ala Phe Glu Gly Val Val Arg Ala
                245                 250                 255

Leu Leu Gln Lys Pro Ser Ala Arg Val Ala Val Leu Phe Thr Arg Ser
            260                 265                 270

Glu Asp Ala Arg Glu Leu Leu Ala Ala Ser Gln Arg Leu Asn Ala Ser
        275                 280                 285

Phe Thr Trp Val Ala Ser Asp Gly Trp Gly Ala Leu Glu Ser Val Val
290                 295                 300

Ala Gly Ser Glu Gly Ala Ala Glu Gly Ala Ile Thr Ile Glu Leu Ala
305                 310                 315                 320

Ser Tyr Pro Ile Ser Asp Phe Ala Ser Tyr Phe Gln Ser Leu Asp Pro
                325                 330                 335

Trp Asn Asn Ser Arg Asn Pro Trp Phe Arg Glu Phe Trp Glu Gln Arg
            340                 345                 350

Phe Arg Cys Ser Phe Arg Gln Arg Asp Cys Ala Ala His Ser Leu Arg
        355                 360                 365

Ala Val Pro Phe Glu Gln Glu Ser Lys Ile Met Phe Val Val Asn Ala
370                 375                 380

Val Tyr Ala Met Ala His Ala Leu His Asn Met His Arg Ala Leu Cys
385                 390                 395                 400

Pro Asn Thr Thr Arg Leu Cys Asp Ala Met Arg Pro Val Asn Gly Arg
                405                 410                 415
```

```
Arg Leu Tyr Lys Asp Phe Val Leu Asn Val Lys Phe Asp Ala Pro Phe
            420                 425                 430

Arg Pro Ala Asp Thr His Asn Glu Val Arg Phe Asp Arg Phe Gly Asp
            435                 440                 445

Gly Ile Gly Arg Tyr Asn Ile Phe Thr Tyr Leu Arg Ala Gly Ser Gly
            450                 455                 460

Arg Tyr Arg Tyr Gln Lys Val Gly Tyr Trp Ala Glu Gly Leu Thr Leu
465                 470                 475                 480

Asp Thr Ser Leu Ile Pro Trp Ala Ser Pro Ser Ala Gly Pro Leu Pro
            485                 490                 495

Ala Ser Arg Cys Ser Glu Pro Cys Leu Gln Asn Glu Val Lys Ser Val
            500                 505                 510

Gln Pro Gly Glu Val Cys Cys Trp Leu Cys Ile Pro Cys Gln Pro Tyr
            515                 520                 525

Glu Tyr Arg Leu Asp Glu Phe Thr Cys Ala Asp Cys Gly Leu Gly Tyr
            530                 535                 540

Trp Pro Asn Ala Ser Leu Thr Gly Cys Phe Glu Leu Pro Gln Glu Tyr
545                 550                 555                 560

Ile Arg Trp Gly Asp Ala Trp Ala Val Gly Pro Val Thr Ile Ala Cys
            565                 570                 575

Leu Gly Ala Leu Ala Thr Leu Phe Val Leu Gly Val Phe Val Arg His
            580                 585                 590

Asn Ala Thr Pro Val Val Lys Ala Ser Gly Arg Glu Leu Cys Tyr Ile
            595                 600                 605

Leu Leu Gly Gly Val Phe Leu Cys Tyr Cys Met Thr Phe Ile Phe Ile
            610                 615                 620

Ala Lys Pro Ser Thr Gly Val Cys Ala Leu Arg Arg Leu Gly Val Gly
625                 630                 635                 640

Thr Ala Phe Ser Val Cys Tyr Ser Ala Leu Leu Thr Lys Thr Asn Arg
            645                 650                 655

Ile Ala Arg Ile Phe Gly Gly Ala Arg Glu Gly Ala Gln Arg Pro Arg
            660                 665                 670

Phe Ile Ser Pro Ala Ser Gln Val Ala Ile Cys Leu Ala Leu Ile Ser
            675                 680                 685

Gly Gln Leu Leu Ile Val Val Ala Trp Leu Val Val Glu Ala Pro Gly
            690                 695                 700

Thr Gly Lys Glu Thr Ala Pro Glu Arg Glu Val Val Thr Leu Arg
705                 710                 715                 720

Cys Asn His Arg Asp Ala Ser Met Leu Gly Ser Leu Ala Tyr Asn Val
            725                 730                 735

Leu Leu Ile Ala Leu Cys Thr Leu Tyr Ala Phe Lys Thr Arg Lys Cys
            740                 745                 750

Pro Glu Asn Phe Asn Glu Ala Lys Phe Ile Gly Phe Thr Met Tyr Thr
            755                 760                 765

Thr Cys Ile Ile Trp Leu Ala Phe Leu Pro Ile Phe Tyr Val Thr Ser
            770                 775                 780

Ser Asp Tyr Arg Val Gln Thr Thr Met Cys Val Ser Val Ser Leu
785                 790                 795                 800

Ser Gly Ser Val Val Leu Gly Cys Leu Phe Ala Pro Lys Leu His Ile
            805                 810                 815

Ile Leu Phe Gln Pro Gln Lys Asn Val Val Ser His Arg Ala Pro Thr
            820                 825                 830
```

```
Ser Arg Phe Gly Ser Ala Ala Ala Arg Ala Ser Ser Ser Leu Gly Gln
        835                 840                 845

Gly Ser Gly Ser Gln Phe Val Pro Thr Val Cys Asn Gly Arg Glu Val
        850                 855                 860

Val Asp Ser Thr Thr Ser Ser Leu
865                 870
```

(2) INFORMATION FOR SEQ ID NO:3:

(i) SEQUENCE CHARACTERISTICS:
        (A) LENGTH: 2619 base pairs
        (B) TYPE: nucleic acid
        (C) STRANDEDNESS: single
        (D) TOPOLOGY: linear (ii) MOLECULE TYPE: mRNA (xi) SEQUENCE DESCRIPTION: SEQ ID NO:3:

```
AUGGGAUCGC UGCUUGCGCU CCUGGCACUG CUGCCGCUGU GGGGUGCUGU GGCUGAGGGC      60

CCAGCCAAGA AGGUGCUGAC CUGGAGGGA GACUUGGUGC UGGUGGGCU GUUCCCAGUG       120

CACCAGAAGG GCGGCCCAGC AGAGGACUGU GGUCCUGUCA AUGAGCACCG UGGCAUCCAG     180

CGCCUGGAGG CCAUGCUUUU UGCACUGGAC CGCAUCAACC GUGACCCGCA CCUGCUGCCU     240

GGCGUGCGCC UGGGUGCACA CAUCCUCGAC AGUUGCUCCA AGGACACACA UGCGCUGGAG     300

CAGGCACUGG ACUUUGUGCG UGCCUCACUC AGCCGUGGUG CUGAUGGCUC ACGCCACAUC     360

UGCCCCGACG GCUCUUAUGC GACCCAUGGU GAUGCUCCCA CUGCCAUCAC UGGUGUUAUU     420

GGCGGUUCCU ACAGUGAUGU CUCCAUCCAG GUGGCCAACC UCUUGAGGCU AUUUCAGAUC     480

CCACAGAUUA GCUACGCCUC UACCAGUGCC AAGCUGAGUG ACAAGUCCCG CUAUGACUAC     540

UUUGCCCGCA CAGUGCCUCC UGACUUCUUC CAAGCCAAGG CCAUGGCUGA GAUUCUCCGC     600

UUCUUCAACU GGACCUAUGU GUCCACUGUG GCGCUCGAGG GCGACUAUGG CGAGACAGGC     660

AUUGAGGCCU UGAGCUAGA GGCUCGUGCC CGCAACAUCU GUGUGGCCAC CUCGGAGAAA     720

GUGGGCCGUG CCAUGAGCCG CGCGGCCUUU GAGGGUGUGG UGCGAGCCCU GCUGCAGAAG     780

CCCAGUGCCC GCGUGGCUGU CCUGUUCACC CGUUCUGAGG AUGCCCGGGA GCUGCUUGCU     840

GCCAGCCAGC GCCUCAAUGC CAGCUUCACC UGGGUGGCCA GUGAUGGUUG GGGGGCCCUG     900

GAGAGUGUGG UGGCAGGCAG UGAGGGGGCU GCUGAGGGUG CUAUCACCAU CGAGCUGGCC     960

UCCUACCCCA UCAGUGACUU UGCCUCCUAC UUCCAGAGCC UGGACCCUUG GAACAACAGC    1020

CGGAACCCCU GGUUCCGUGA AUUCUGGGAG CAGAGGUUCC GCUGCAGCUU CCGGCAGCGA    1080

GACUGCGCAG CCCACUCUCU CCGGGCUGUG CCCUUUGAGC AGGAGUCCAA GAUCAUGUUU    1140

GUGGUCAAUG CAGUGUACGC CAUGGCCCAU GCGCUCCACA ACAUGCACCG UGCCCUCUGC    1200

CCCAACACCA CCCGGCUCUG UGACGCGAUG CGGCCAGUUA ACGGGCGCCG CCUCUACAAG    1260

GACUUUGUGC UCAACGUCAA GUUUGAUGCC CCCUUCGCC CAGCUGACAC CCACAAUGAG    1320

GUCCGCUUUG ACCGCUUUGG UGAUGGUAUU GGCCGCUACA ACAUCUUCAC CUAUCUGCGU    1380

GCAGGCAGUG GGCGCUAUCG CUACCAGAAG GUGGGCUACU GGGCAGAAGG CUUGACUCUG    1440

GACACCAGCC UCAUCCCAUG GGCCUCACCC UCAGCCGGCC CCCUGCCCGC CUCUCGCUGC    1500

AGUGAGCCCU GCCUCCAGAA UGAGGUGAAG AGUGUGCAGC CGGGCGAAGU CUGCUGCUGG    1560

CUCUGCAUUC CGUGCCAGCC CUAUGAGUAC CGAUUGGACG AAUUCACUUG CGCUGAUUGU    1620

GGCCUGGGCU ACUGGCCCAA UGCCAGCCUG ACUGGCUGCU UCAACUGCC CCAGGAGUAC    1680

AUCCGCUGGG GCGAUGCCUG GGCUGUGGGA CCUGUCACCA UCGCCUGCCU CGGUGCCCUG    1740
```

```
                                                              -continued

GCCACCCUCU UUGUGCUGGG UGUCUUUGUG CGGCACAAUG CCACACCAGU GGUCAAGGCC    1800

UCAGGUCGGG AGCUCUGCUA CAUCCUGCUG GGUGGUGUCU UCCUCUGCUA CUGCAUGACC    1860

UUCAUCUUCA UUGCCAAGCC AUCCACGGGA GUGUGUGCCU UACGGCGUCU UGGGGUGGGC    1920

ACUGCCUUCU CUGUCUGCUA CUCAGCCCUG CUCACCAAGA CCAACCGCAU UGCACGCAUC    1980

UUCGGUGGGG CCCGGGAGGG UGCCCAGCGG CCACGCUUCA UCAGUCCUGC CUCACAGGUG    2040

GCCAUCUGCC UGGCACUUAU CUCGGGCCAG CUGCUCAUCG UGGUCGCCUG GCUGGUGGUG    2100

GAGGCACCGG GCACAGGCAA GGAGACAGCC CCCGAACGGC GGGAGGUGGU GACACUGCGC    2160

UGCAACCACC GCGAUGCAAG UAUGUUGGGC UCGCUGGCCU ACAAUGUGCU CCUCAUCGCG    2220

CUCUGCACGC UUUAUGCCUU CAAGACUCGC AAGUGCCCCG AAAACUUCAA CGAGGCCAAG    2280

UUCAUUGGCU UCACCAUGUA CACCACCUGC AUCAUCUGGC UGGCAUUCUU GCCCAUCUUC    2340

UAUGUCACCU CCAGUGACUA CCGGGUACAG ACCACCACCA UGUGCGUGUC AGUCAGCCUC    2400

AGCGGCUCCG UGGUGCUUGG CUGCCUCUUU GCGCCCAAGC UGCACAUCAU CCUCUUCCAG    2460

CCGCAGAAGA ACGUGGUUAG CCACCGGGCA CCCACCAGCC GCUUUGGCAG UGCUGCUGCC    2520

AGGGCCAGCU CCAGCCUUGG CCAAGGGUCU GGCUCCCAGU UUGUCCCCAC UGUUUGCAAU    2580

GGCCGUGAGG UGGUGGACUC GACAACGUCA UCGCUUUGA                          2619
```